United States Patent [19]

Miller

[11] Patent Number: 5,610,027
[45] Date of Patent: Mar. 11, 1997

[54] MICROPHOTO LYSIS-ANLAYSIS PROCESS TO MEASURE CELL CHARACTERISTICS

[75] Inventor: Frederick N. Miller, Louisville, Ky.

[73] Assignee: Micro-Med, Inc., Louisville, Ky.

[21] Appl. No.: 969,764

[22] Filed: Oct. 30, 1992

[51] Int. Cl.$^6$ .................................................. C12Q 1/02
[52] U.S. Cl. ............................. 435/29; 435/7.2; 436/10; 436/63; 436/172; 436/902; 422/55; 422/73; 324/71.4; 324/71.1
[58] Field of Search .......................... 435/29, 7.2, 34, 435/70.4; 436/63, 17, 164, 172, 519, 902, 10; 422/55, 82.05, 73, 82.07; 324/71.1, 71.4

[56] References Cited

U.S. PATENT DOCUMENTS

| | | | |
|---|---|---|---|
| 3,882,385 | 5/1975 | Coulter et al. | 324/71.1 |
| 4,220,916 | 9/1980 | Zimmermann et al. | 324/71.1 |
| 4,278,936 | 7/1981 | Shine | 324/71.1 |
| 4,374,644 | 2/1983 | Armstrong | 436/63 |
| 4,491,012 | 1/1985 | Peterson | 73/61.4 |
| 4,535,284 | 8/1985 | Groves et al. | 324/71.1 |
| 4,599,307 | 7/1986 | Saunders et al. | 435/34 |
| 4,656,139 | 4/1987 | Matsuda et al. | 436/17 |
| 4,657,851 | 4/1987 | Feller et al. | 435/7 |
| 4,797,606 | 1/1989 | Jahn et al. . | |
| 4,835,457 | 5/1989 | Hanss et al. | 324/71.4 |
| 4,882,284 | 11/1989 | Kirchanski et al. | 436/63 |
| 5,057,413 | 10/1991 | Terstappen et al. | 435/6 |
| 5,128,245 | 7/1992 | Greenberg et al. | 435/29 |

FOREIGN PATENT DOCUMENTS 0209526  5/1984  Germany .............................. 324/71.1

OTHER PUBLICATIONS

Artmann, G. A microscopic photometric method for measuring erythrocyte deformability. Clinical Hemorheology 6:617–627, 1986.

Blum, H.F. Photodynamic Hemolysis; II. Modes of inhibition. Journal of Cellular and Comparative Physiology 9:229–239, 1937.

Blum, H.F. and J.L. Morgan. Photodynamic Hemolysis: III. The percentage hemolysis curve. Journal of Cellular and Comparative Physiology 13:269–279, 1939.

Clark, M.R., N. Mohandas, and S.B. Shohet. Osmotic gradient ektcytometry: Comprehensive characterization of red cell volume and surface maintenance. Blood 61:899–910, 1983.

Cummings, D.M. and S.K. Ballas. Effects of pentoxifylline and metabolite on red blood cell deformability as measured by ektacytometry. Angiology 41:118–123, 1990.

Deuticke, B., B. Poser, P. Lutkemeier, and C.W.M. Haest. Formation of aqueous pores in the human erythrocyte membrane after oxidative cross–linking of spectrin by diamide. Biochim. et. Biophys. Acta. 731:196–210, 1983.

Deuticke, B., P. Lutkemeier, and M. Sistemich. Ion selectivity of aqueous leaks in the erythrocyte membrane by cross–linking of membrane proteins. Biochimica et Biophysica Acta. 775:150–160, 1984.

Dougherty, T.J. Photosensitizers: Therapy and detection of malignant tumors. Photochem. Photobiol. 45:879–889, 1987.

Fleischer, A.S., B.S. Leonard, C. Harper, J.S. Cook, and R.L. Baer. Mechanism of in vivo photohemolysis in erythropoietic protoporphyria. J. Invest. Dermatol. 46:505–509, 1966.

(List continued on next page.)

Primary Examiner—James C. Housel
Assistant Examiner—Harold Y. Pyon
Attorney, Agent, or Firm—Middleton & Reutlinger; David W. Carrithers

[57] ABSTRACT

A method of determining cell membrane strength is disclosed, using focused light of selected frequency and energy density. The method is also useful in diagnosing the presence of certain diseases in cells, by comparing the membrane strength of cells exposed to cell-characteristic altering drugs to the membrane strength of a control group of cells.

70 Claims, 22 Drawing Sheets

OTHER PUBLICATIONS

Girotti, A.W. Photodynamic lipid peroxidation in biological systems. Photochemistry and Photobiology 51:497–509, 1990.

Kuwabara, M., T. Yamamoto, O. Inanami, and F. Sato. Mechanisms of photosensitization by pheophorbide as studied by photohemolysis of erythrocytes and electron spin resonance spectroscopy. Photochem. and Photobiol. 49:37–41, 1989.

Lipowsky, H.H., S. Usami, and S. Chien. Human SS red cell rheological behavior in microcirculation of the cremaster muscle. Blood Cells 8:113–126, 1982.

Mayhan, W.G. and W.L. Joyner. The Effects of altering the external calcium concentration and a calcium channel blocker, verapamil, on microvascular leaky sites and dextran clearance in the hamster cheek pouch. Microvasc. Res. 28:159–179, 1984.

Messmann, R., S. Gannon, S. Sarnaik, and R.M. Johnson. Mechanical Properties of Sickle Cell Membranes. Blood 75:1711–1717, 1990.

Minetti, M. and A.M.M. DiStasi. Involvement of erythrocyte skeletal proteins in the modulation of membrane fluidity by phenothiazines. Biochemistry 26:8133–8137, 1987.

Mohandas, N., J.A. Chasis, and S.B. Shohet. The influence of membrane skeleton on red cell deformability, membrane material properties and shape. Seminars in Hamatlogy 20:225–242, 1983.

Mohandas, N., M.R. Clark, M.S. Jacobs, and S.B. Shohet. Analysis of factors regulating erythrocyte deformability. J. Clin. Invest. 66:563–573, 1980.

Pooler, J.P. and A.W. Girotti. Photohemolysis of human erythrocytes labeled in band 3 with eosin–isothiocyanate. Photochemistry and Photobiology 44:495–499, 1986.

Quist, E. and P. Powell. Polyphosphoinositides and the shape of mammalian erythrocytes. Lipids 20:433–438, 1985.

Reinhart, W.H. and S. Chien. The time course of filtration test as a model for microvascular plugging by white cells and hardened red cells. Microvasc. Res. 34:1–12, 1987.

Rosso, J., A. Zachowski, and P.F. Devaux. Influence of chlorpromazine on the transverse mobility of phospholipids in the human erythrocyte membrane: relation to shape changes. Biochimica et Biophysica Acta. 942:271–279, 1988.

Schothorst, A.A., J. van Steveninck, L.N. Went, and D. Suurmond. Metabolic aspects of the photodynamic effect of protoporphyrin in protoporphyria and in normal red blood cells. Clin. Chim. Acta. 33:207–213, 1971.

Valenzeno, D.P., and J.W. Trank. Measurement of cell lysis by light scattering. Photochem. and Photobiol. 42:335–339, 1985.

Valenzeno, D.P. Photomodification of biological membranes with emphasis on singlet oxygen mechanisms. Photochemistry and Photobiology 46:147–160, 1987.

Verweij, H., T.M.A.R. Dubbelman, and D.J. van Steveninck. Photodynamic protein cross–linking. Biochimica et Biophysica Acta 646:87–94, 1981.

Quantitation of Erythrocyte Photohemolysis by Light Microscopy by Fred Miller, G. Taupelder, & D. Slaat, & R. Rewenaur *Blood Cells*.

"Use of Microphotokenolysis to Distinguish Differences in Erythrocyte Treatments", by Fred Miller, G. Taupelder; D. Slack, & R. Renauer, in *Blood Cells*.

Cummings et al, Effects of pentoxifylline and metabolite on red blood cell deformability as measured by ektacytometry Angiology 41:118–123, 1990.

Minetti et al, Involvement of erythrocyte skeletal proteins in the modulation of membrane fluidity by phenothiazines. Biochemistry 26:8133–8137, 1987.

5,610,027

MICROPHOTO LYSIS-ANLAYSIS PROCESS TO MEASURE CELL CHARACTERISTICS

BACKGROUND OF THE INVENTION

Most biological cells can drastically change their shape (called cell deformability) without a change in the functional integrity of the cell membrane. Under certain conditions, the cell membrane can rupture to lose cell contents (called cell fragility). Cells can have any combination of a high-to-low deformability and a high-to-low fragility. However, most cells normally have high deformability and moderate-to-low fragility.

Deformability is an important characteristic for function of some normally stationary cells such as "sensory receptors" and normally moving cells such as blood and lymph cells. Cell fragility is an important characteristic for almost all body cells because changes in the cell environment can shift water into a cell to rupture fragile cells. Thus, changes in cell fragility can also change the ability of a cell to perform its normal function. For example, an abnormally high fragility to rupture part of the circulating pool of red blood cells will reduce the transport of oxygen to tissues. Thus, fragility might clinically be a more important cell characteristic than deformability.

Cell fragility changes with cell age, duration of blood-bank storage, treatment with a variety of membrane-binding drugs, and progression of membrane or hemoglobin-related diseases such as sickle-cell anemia and diabetes. Thus, a rapid, highly accurate, and easily applied method is needed for clinical measurements to assess cell fragility as an index of cell ability to function (called cell integrity). The current methods use mechanical forces primarily to assess the deformability or fragility of red blood cells. These current methods include Osmotic-Gradient Ektacytometry, Filtration, Micropipette Suction, and Osmotic Fragility. Of these, only the Osmotic Fragility method is commonly used in clinical laboratories.

Osmotic-Gradient Ektacytometry is one technology that has been developed to measure cell deformability. This technology uses a viscometer to measure shape changes which are induced in red blood cells by different osmotic solutions at various levels of rotational speed (called applied shear stress). The use of different osmotic solutions offers the potential for this Ektacytometry method to determine several properties which could influence the deformability of red blood cells. However, the osmotic-spectrum curves which are produced by Ektacytometry are complex and very difficult to interpret. These curves are also subject to high variability due to changes in sample ambient temperature, pH, and plasma osmolality. Thus, Ektacytometry currently requires very sophisticated equipment, extensive operator training, and highly controlled test conditions to make it usable, but only in a few research laboratories and not in the clinical setting.

Other methods for measuring cell deformability include filtration through various size pores, aspiration of cells into micropipettes of fixed tip size and taper, and a photometric technique. All of these methods also require very sophisticated equipment and substantial operator training; and they are extremely time consuming for analysis of relatively few cells in a few samples. Thus, these methods have also not been accepted into general clinical use.

Impedance measurements (Hands et al, U.S. Pat. No. 4,835,457) and time measurements (David D. Paterson, U.S. Pat. No. 4,491,012) have been made on red cells that pass under pressure through a membrane or a foil system (Helmut Jahn, U.S. Pat. No. 4,797,606) as variations of the Filtration method for measurement of cell deformability. These variations are extremely sensitive to manufacturing tolerances on the filter or foil and they primarily measure only deformability rather than cell fragility. Thus, these variant Filtration methods have also not been accepted into common clinical use.

The Osmotic Fragility test was one of the earliest methods that was developed for assessment of red blood cell integrity, and it is one of the few tests currently in clinical use. The Osmotic Fragility test is time-consuming, requires multiple blood handling steps, usually requires relatively large blood samples, and provides no information about the lysis (cell membrane disruption) rate. These limitations and the lack of sensitivity to mild or moderate changes in cell fragility has often led to the clinical use of this osmotic test only for diagnosis of one disease called hereditary spherocytosis.

It was first shown some fifty years ago that some chemicals can be changed by light (called photoactivation) to induce the rupture or breakup of red blood cells (called hemolysis) in a test tube. Since then, this basic process (called photohemolysis) has been extensively studied in a variety of test-tube experiments.

The mechanism for photohemolysis is oxygen dependent and probably involves the generation of singlet oxygen with the subsequent oxidation of proteins in the red blood cell membrane. This protein oxidation leads to the creation of water channels with an increase in passive cationic exchange and the subsequent influx of water into the cell to produce hemolysis. Photohemolysis could also involve peroxidation of the lipid layers of the cell membrane. This peroxidation would alter membrane fluidity in the lipid bilayer to limit the ability of the cell to undergo shape changes, which are dependent on changes in the lipid bilayer.

Thus, there is considerable scientific evidence to show that certain chemical agents can be photoactivated to disrupt red blood cells by altering either the protein or the lipid layer of the cell membrane. These membrane alterations disrupt membrane integrity to permit water inflow which changes cell shape (called cell deformability) by increasing cell volume until the "internal cell pressure" breaks the cell membrane (called cell fragility) sufficiently to permit loss of cell contents (called lysis or hemolysis in the case of red blood cells).

Current clinical methods use milliliter quantities of blood solutions to measure the osmolality (equivalent to internal water pressure) at which hemolysis occurs. However, these hemolysis methods cannot separate changes in deformability from those in fragility, cannot distinguish between loss of membrane integrity due to protein layer changes and that due to lipid layer changes, and cannot determine "rates of hemolysis" to provide a more sensitive hemolysis test for clinical use.

Current clinical methods are "macro" techniques in that relatively large blood volumes (milliliter quantities) are exposed to various osmotic solutions to determine hemolysis. These Osmotic Fragility tests are generally performed in relatively large test tubes or cuvettes using parallel light for activation. Likewise, current photohemolysis research methods are also "macro" techniques in that milliliter quantities of blood are exposed to photoactivation, and long analysis times are required to obtain a single measurement. Photoactivation of red blood cells incubated with 0.1 mM of protoporphyrin as a "cell-attack" agent requires about twenty minutes of illumination time to achieve a modest 20% hemolysis while a 100% hemolysis requires a 25-minute or longer exposure. Similarly, more than twenty minutes of light exposure is needed with pheophorbide as the cell-attack agent to give about a 90% hemolysis. Light exposures of 3–4 hours are needed with eosin-isothiocyanate as the cell-attack agent to give maximal hemolysis which occurs about 11 hours after photoactivation. All of these current methods require extended time periods primarily because they use unfocused light which limits the activation to low light power densities.

All of the current Osmotic Fragility and Photohemolysis methods require multiple dilutions, centrifugation, and analysis in a spectrophotometer to give single measurements of a percent cell hemolysis. Thus, the current clinical and research methods are time consuming, and simultaneous light-dose and time-dependent relationships are next-to-impossible to obtain from one blood sample. Some researchers have used a light scattering device to detect photohemolysis. However, this device is very sensitive to very small changes in red blood cell concentrations, and this device requires a monolayer of red blood cells with a red cell concentration of less than 0.00025% which is extremely difficult to achieve even by current micropipetting systems. Even then, this cell monolayer method is quite time-consuming since 100% hemolysis requires 4 hours with phloxinc B as the cell-attack agent.

SUMMARY OF THE INVENTION

The present invention includes a new "microphotolysis" process to apply precise quantities of focused light energy to a precise microscopic area of a very small cell sample (a cell micro-sample of less than 25 µl) to activate a chemical agent which then attacks the nearby cell membranes. The present invention includes a new "microphotoanalysis" process which measures, as a function of time, the precise degree of cell disruption which is caused by the photoactivated chemical in the microscopic area of cell-attack. This procedure gives a quantitative, time-related, light-dose dependent measure of cell fragility.

The present invention (called the Microphoto Lysis-Analysis process) has several advantages over other current methods which give relatively imprecise estimates of cell deformability or cell fragility. The Microphoto Lysis-Analysis process uses focused light to activate the cell-attack chemical only in a very small defined area of a cell micro-sample. Thus, multiple micro-sample area can be used to obtain multiple photoactivations with one area as an unactivated control in a single micro-sample. Also, each micro-sample area is analyzed before photoactivation to provide its own control value for determination of the lysis response. In contrast to other methods, this multiple-activation self-control feature of the present invention provides an "energy-dose lysis-response" test to give very precise time-related measurements of cell membrane fragility.

Unlike other methods, the use of focused light on a small area of a cell micro-sample in the present invention only requires relatively short photoactivation times of 2 to 10 minutes with a short time, depending on the cell population, of 30 to 60 minutes to complete cell lysis. Thus, the present invention provides a first-ever complete microphotolysis response curve to measure the rate of cell lysis within a total measurement time of less than one hour on a single cell microsample of 25 microliters (µl).

In the present invention, precise quantities (doses) of various drugs can be added to the cell micro-sample to test for the effect (efficacy) of these drugs to improve cell fragility. Thus, the present invention can provide a first-ever complete dose-response analysis for six drug doses on a total blood specimen of 150 µl.

Unlike the other methods, the present invention (new process) requires no further cell manipulation after the microsample is placed in the sample-carrier. The new process is easy to perform with easy-to-conduct tests of reproducibility by repeated photoactivation in a second microsample area. The new process gives a microphotolysis that depends only on the light-activation energy and on the concentration and formulation of the cell-attack chemical. The new process is not complicated (as are other methods) by variations in sample temperature (from the light source) which could increase Brownian cell motion to confound the lysis measurements, or by non-specific effects of other blood constituents such as plasma in the cell micro-sample. Thus, the new process creates a very specific light-related activity only in the area of focused light-activation.

The new process can measure alterations in cell membrane fragility due to changes in membrane characteristics that are created by a cell-attack agent that remains and becomes activated only outside the cell (an extracellular agent). The new process can measure alterations in cell membrane fragility due to changes in internal cell structures that are created by a cell-attack agent that crosses the cell membrane to attach to internal cell structures where the agent becomes photoactivated. Thus, the new process can provide first-ever detection of diseases that alter only the cell membrane, systemic diseases which alter only the internal cell composition, and cell alterations due to drug treatments.

The energy level for activation of an intracellular agent will in part depend on the anti-oxidant status of the cell. Many cells such as red blood cells usually carry oxygen and these cells maintain a well developed anti-oxidant system to protect the cell against auto-oxidation. Other current techniques to assess cell fragility or deformability cannot also assess antioxidant activity because these other methods do not induce oxidation reactions within the cell. The present invention can measure the difference in cell fragility due to photoactivation of specific external and internal chemical agents as a new method to determine the status of the anti-oxidant system in the cell.

The present invention is a new "microphotolysis and microphotoanalysis process" which uses a new combination of generally available equipment in a new sequence of new procedures, solutions, and new preparations.

Accordingly, it is an object of the present invention to provide a new configuration of microscope, light source, light control, television imaging, and video recording equipment to provide cell images at standardized illuminations.

It is a further object of the present invention to provide a new microscope calibration procedure to provide microexposures of cells to quantitated, focused, frequency-specific light energies.

It is a further object of the present invention to utilize a generally known selection procedure to obtain a cell specimen.

It is a further object of the present invention to utilize preparation of a standard buffer solution to provide a standardized environment for the cell specimen.

It is another object of the present invention to provide a new method of use for a new preparation of a fluorochrome solution used for other types of measurements in order to provide a quantifiable new cell-attack stimulus for different microsamples of the cell specimen.

It is yet another object of the present invention to provide a new method for preparation of the cell specimen to give a standardized mixture of cells and cell-attack stimuli in a standardized solution (buffer) environment.

It is a further object of the present invention to provide a new micro-sample preparation for subsequent measurements for cell disruption.

It is a further object of the present invention to provide a new microphotolysis procedure for precision light-stimulated attack to disrupt the cells in the micro-sample in a new standardized manner.

It is yet a further object of the present invention to provide a new procedure for microphotoanalysis of micro-sample images to measure the time-sequenced disruption of cells during light-stimulated cell-attack in small regions of the micro-sample.

These and other improvements will be better understood on reading the description which follows.

BRIEF DESCRIPTION OF THE DRAWINGS

A better understanding of the present invention will be had upon reference to the following description in conjunction with the accompanying drawings, wherein:

FIG. 3 is a plot showing a repeat of the curve (open circles) of FIG. 1 as the graphical basis for definition of:

1) the Maximal Microphotolysis Response (MR) as the zerotime Response-Area Optical Density (ZROD) minus the Minimum Plateau Response-Area Optical Density (PROD);

2) the Percent Maximal Response (MR%) as 100 times MR divided by ZROD; and 3) the % Response at a Specific time t (% Response(t)) as 100 times the quantity, ZROD minus the Response-Area Optical Density at time t (ROD(t)), that resultant quantity divided by MR.

Figure 1:
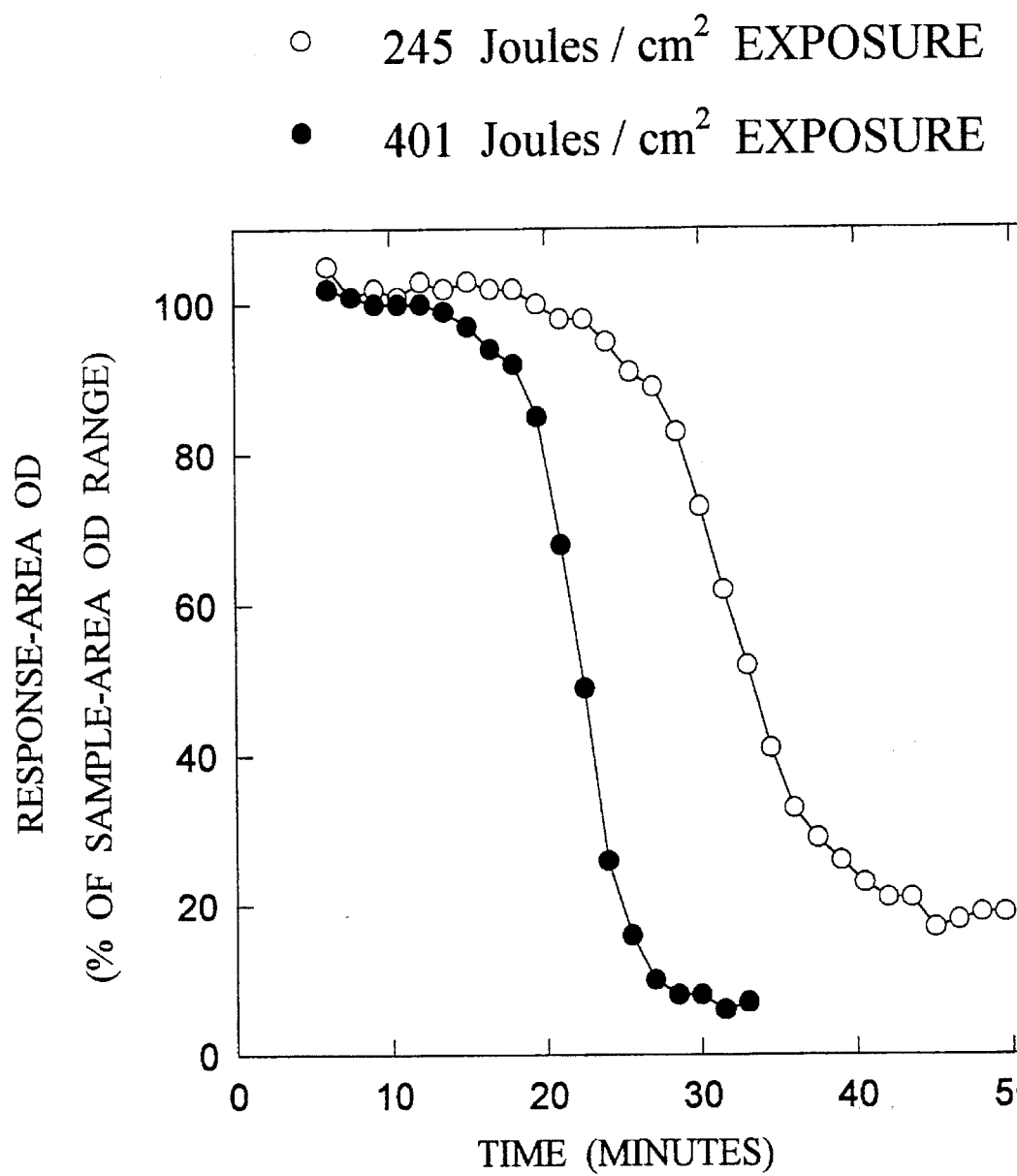
FIG. 1 is a plot showing curves for the percentage number of surviving intact human red blood cells (measured as a relative Response-Area Optical Density) in two rectangular areas of a cell micro-sample as a function of time from the beginning of a light-activated cell-attack stimulus of 245 Joules/cm$^2$ (open circles) which creates microphotolysis in one rectangular area and 401Joules/cm$^2$ (filled circles) which creates microphotolysis in a second rectangular area.
Figure 2:
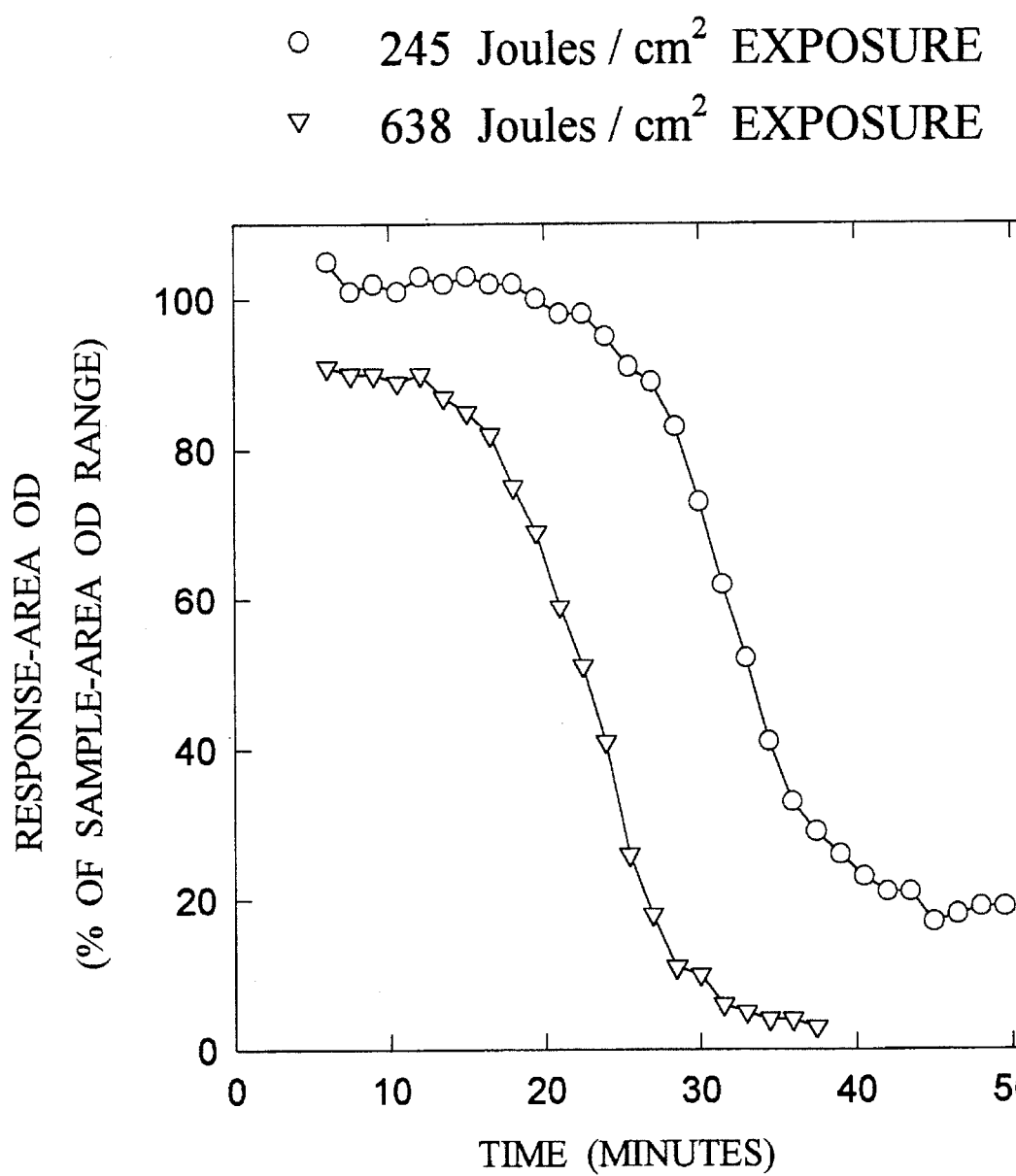
FIG. 2 is a plot showing a repeat of the curve (open circles) of FIG. 1 for the 245 Joules/cm$^2$ stimulus and gives a Response-Area Optical Density curve as a function of time from the beginning of a light-activated cell-attack stimulus of 638 Joules/cm$^2$ (filled circles) to create microphotolysis in a third rectangular area of the cell specimen that gave FIG. 1.
Figure 3:
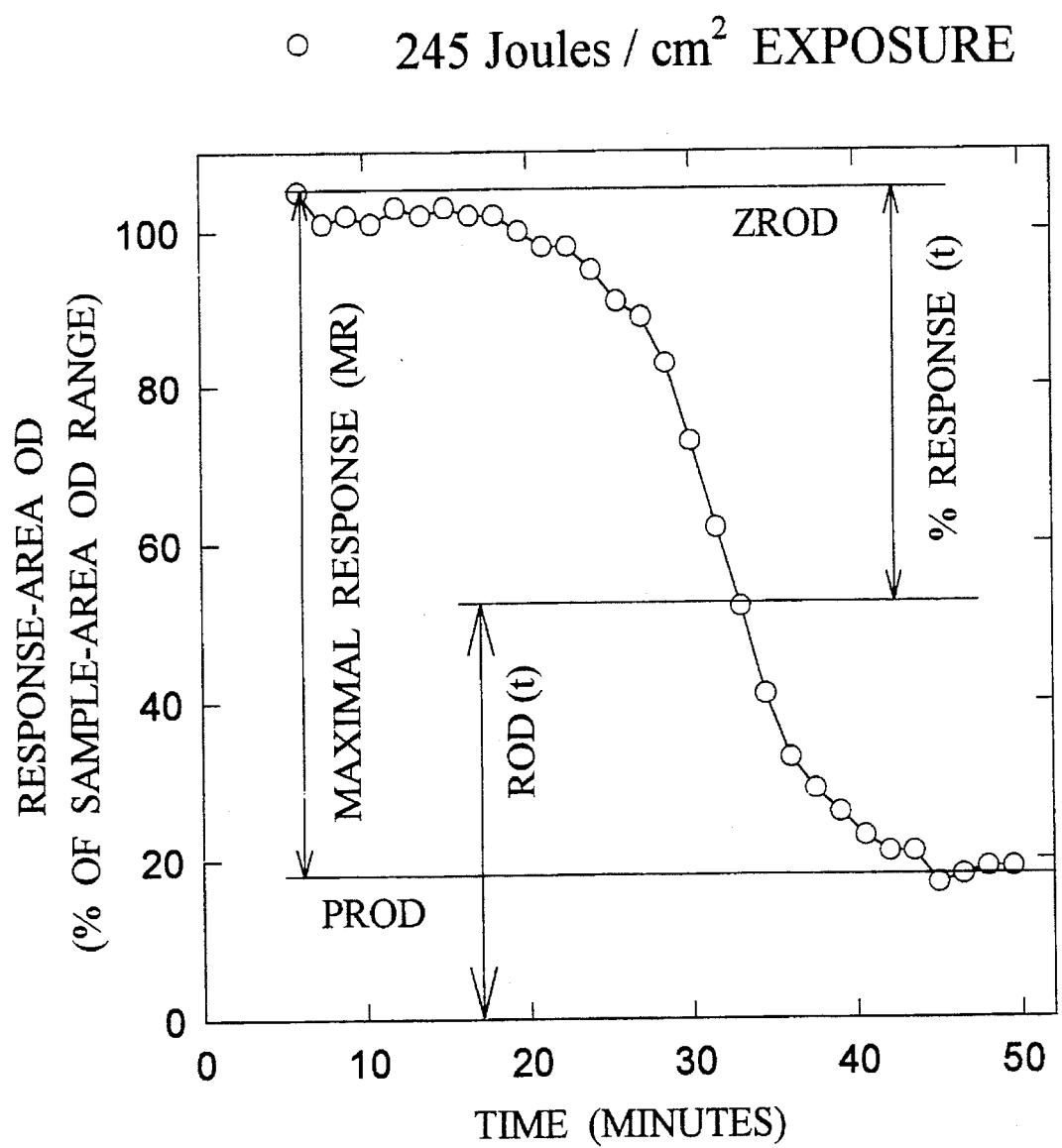
Figure 4:
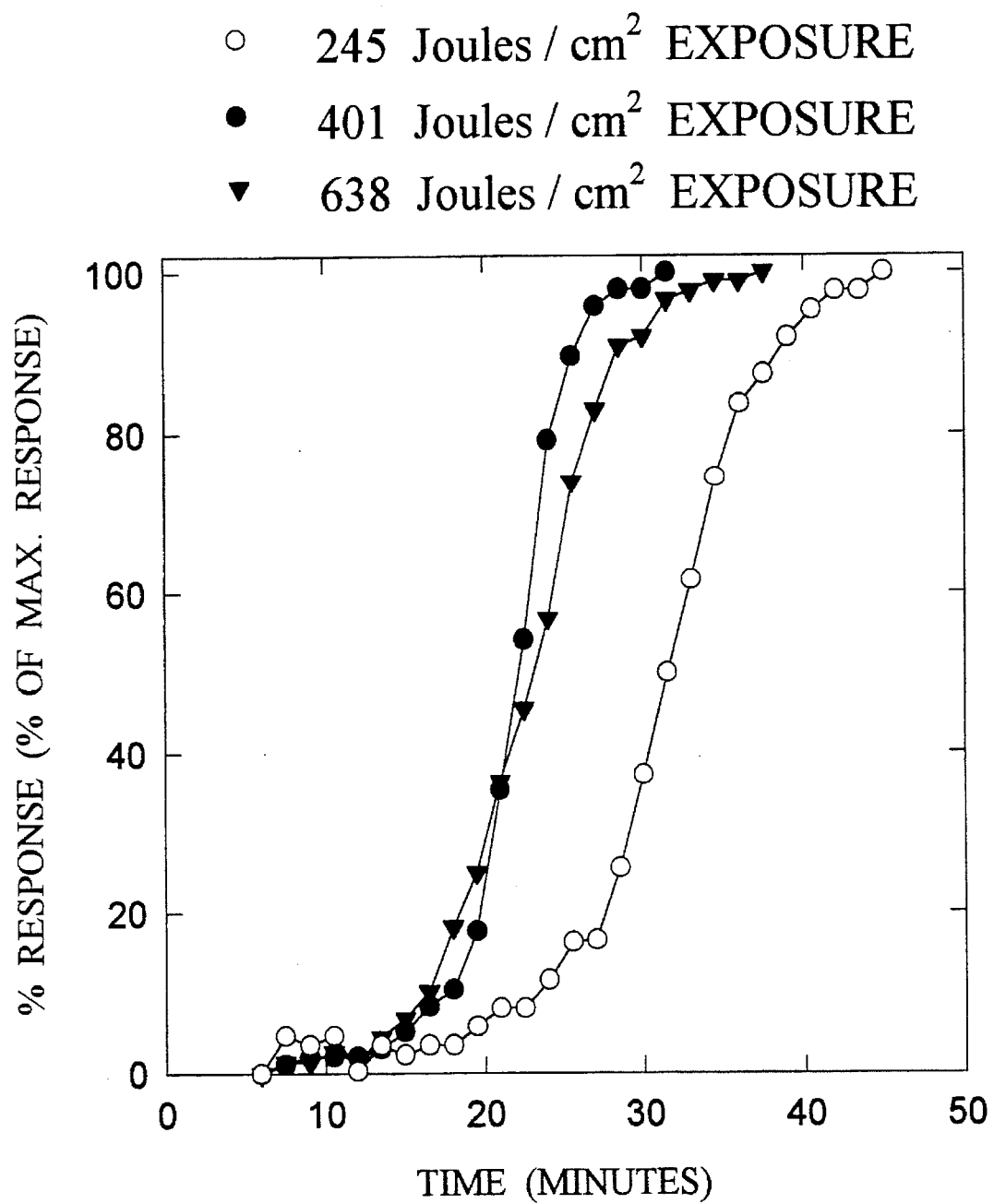

FIG. 4 is a plot showing the three microphotolysis Response curves which are generated by application of the definitions in FIG. 3 to the three Response-Area Optical Density curves in FIG. 1 and FIG. 2.

Figure 5:
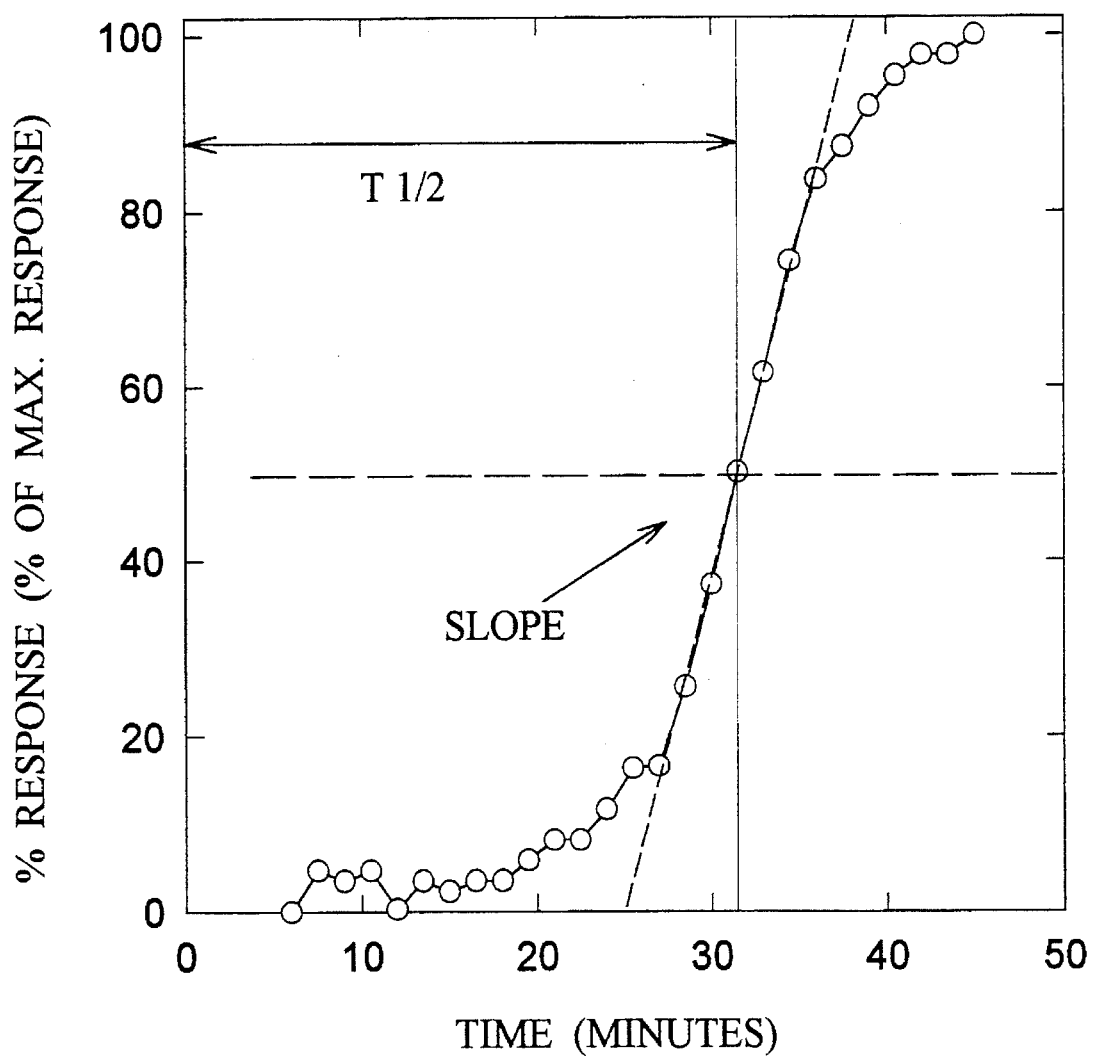

FIG. 5 is a plot showing a repeat of the microphotolysis % Response curve (open circles) of FIG. 4 as the graphical basis for definition of:

1) the response half-time ($T_{1/2}$) as the period from the beginning of cell-attack to the time of the 50-percent response value, and 2) the largest slope of the % Response curve as the Slope at time $t=T_{1/2}$.

Figure 6:
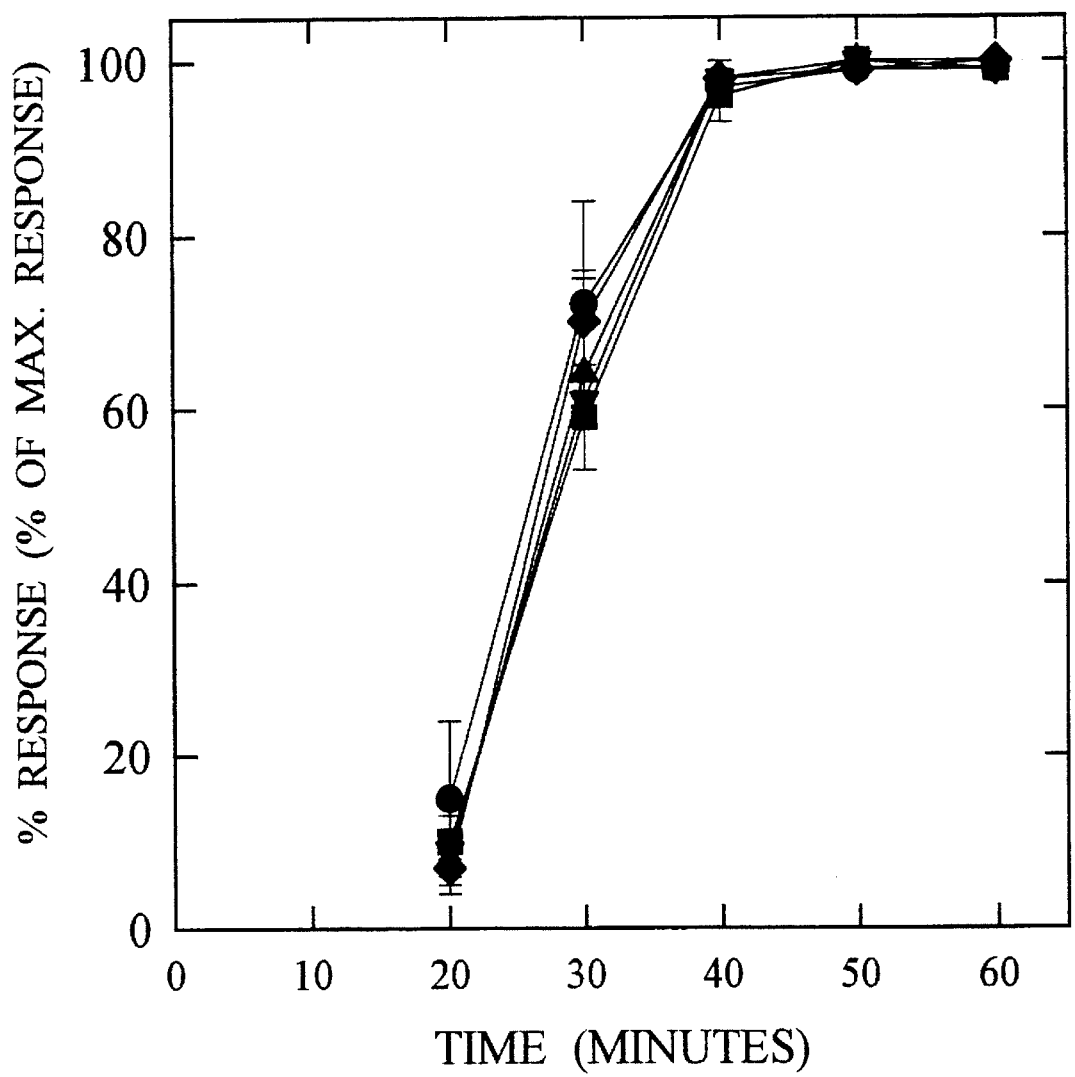

FIG. 6 is a plot showing the % Response curve (mean±SEM) for microphotolysis on day 1 at 7 hours (circles), day 2 (squares), day 3 (triangles), day 4 (diamonds), and day 5 (inverted triangles) after collection of red blood cells from four rabbits.

Figure 7:
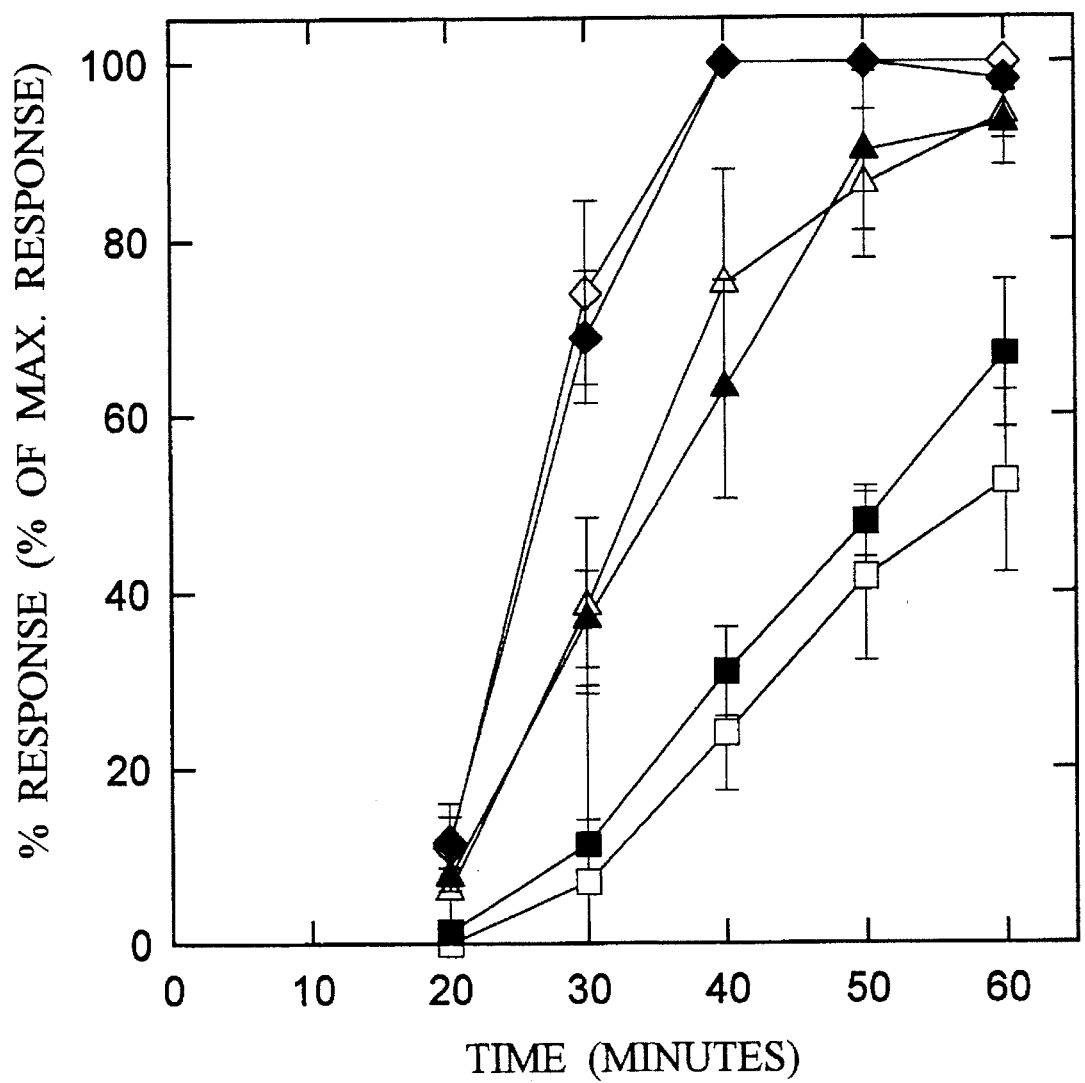

FIG. 7 is a plot showing the % Response curves (mean±SEM) for the effect of cell-attack stimuli of 105 Joules/cm$^2$ (open squares), 126 Joules/cm$^2$ (filled squares), 159 Joules/cm$^2$ (open triangles), 168 J/cm$^2$ (filled triangles), 210 J/cm$^2$ (open diamonds), and 210 J/cm$^2$ (filled diamonds) on rabbit (N=3) red blood cells.

Figure 8:
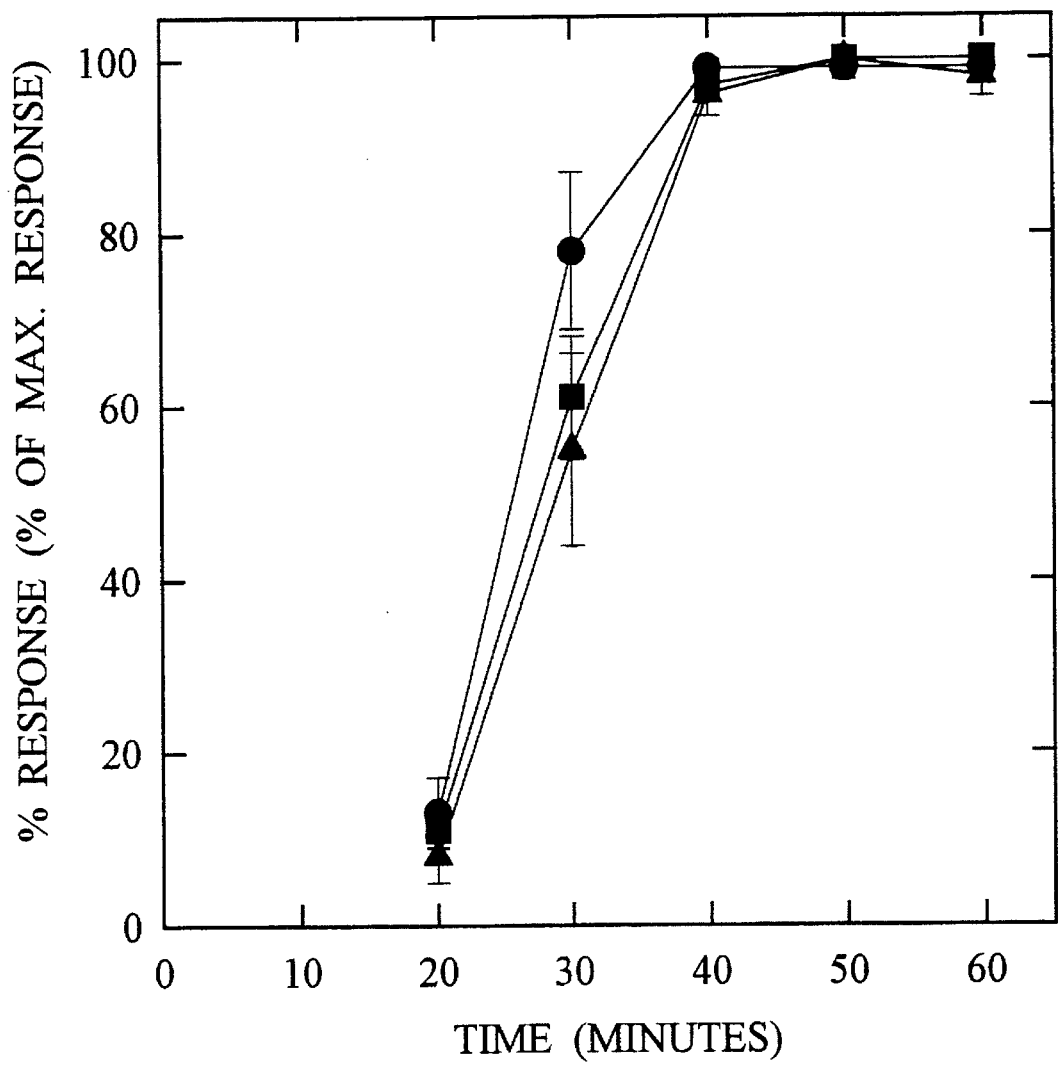

FIG. 8 is a plot showing the % Response curves (mean±SEM) for microphotolysis of 3% (circles), 4% (triangles), and 5% (squares) concentrations of rabbit (N=4) red blood cells.

Figure 9:
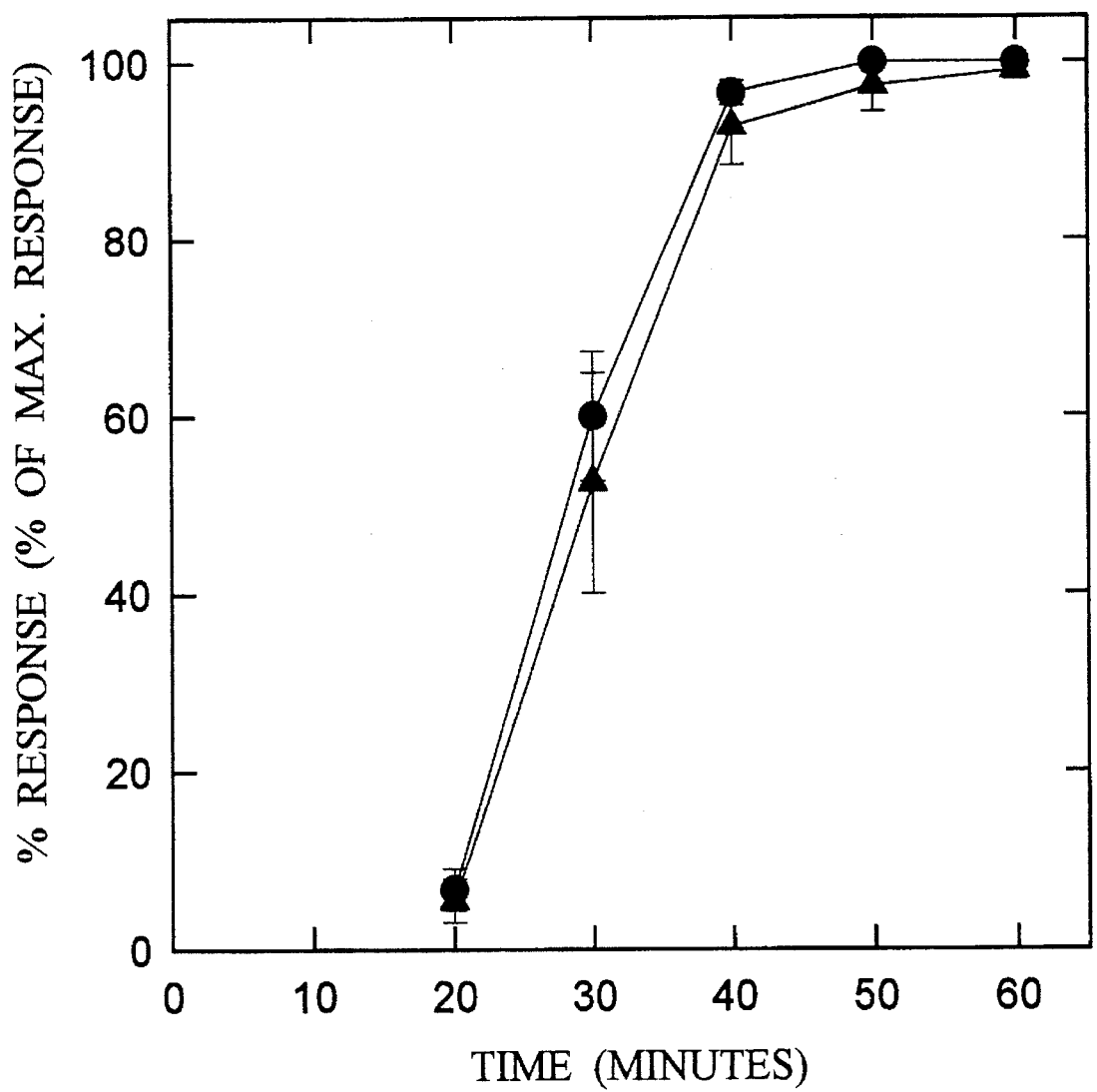

FIG. 9 is a plot showing the % Response curves (mean±SEM) for microphotolysis of rabbit (N=3) red blood cells that had been separated from whole blood (circles) and for red blood cells in whole blood that contained plasma and other cells such as platelets or white blood cells (triangles).

Figure 10:
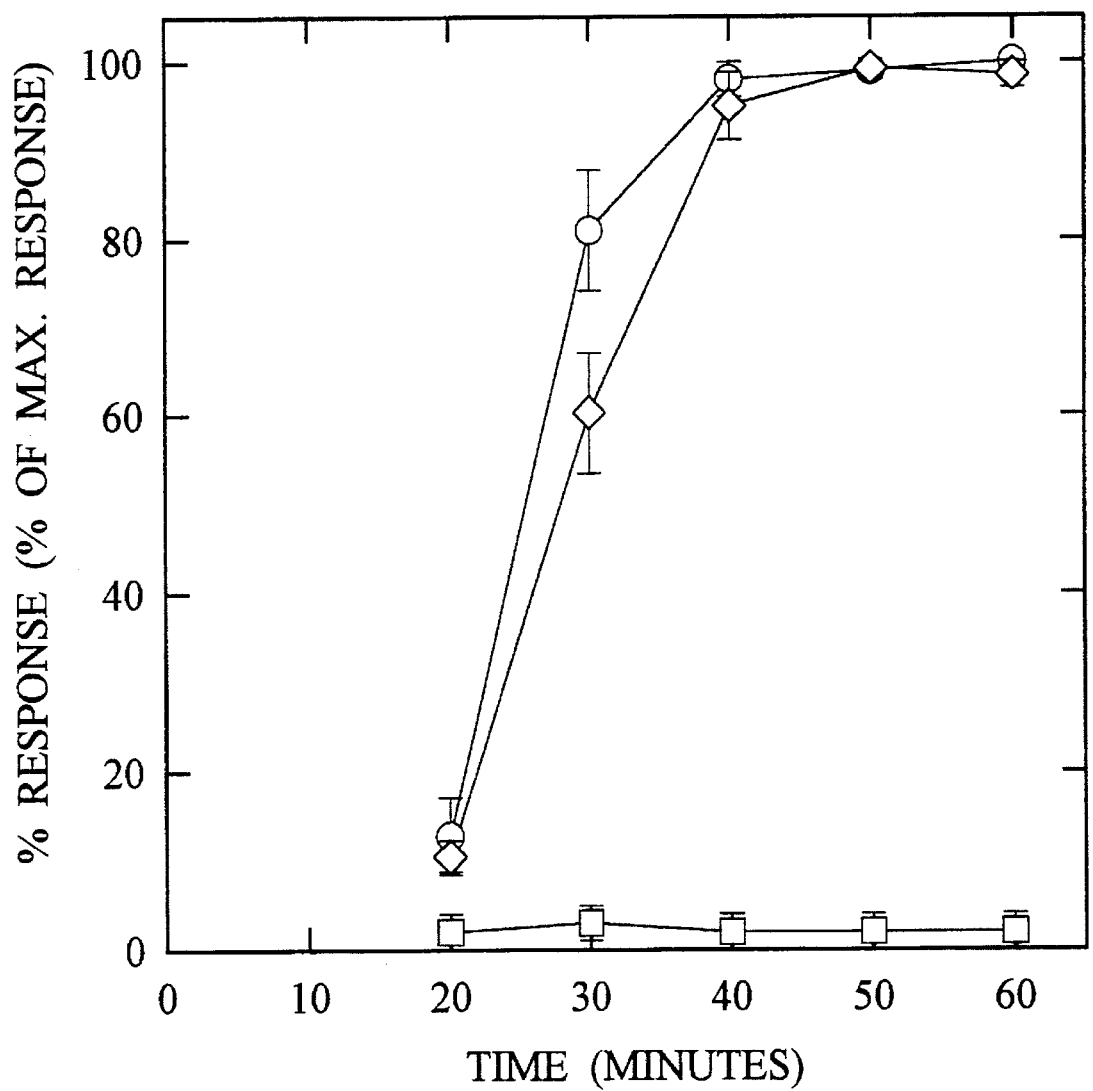

FIG. 10 is a plot showing the % Response curves (mean±SEM) for microphotolysis of rabbit (N=4) red blood cells on day 5 (circles), on day 5 after the red blood cells had been washed and reconstituted with buffer and FITC-dextran (diamonds), and on day 5 after the red blood cells had been washed and reconstituted with buffer but not FITC-dextran (squares).

Figure 11:
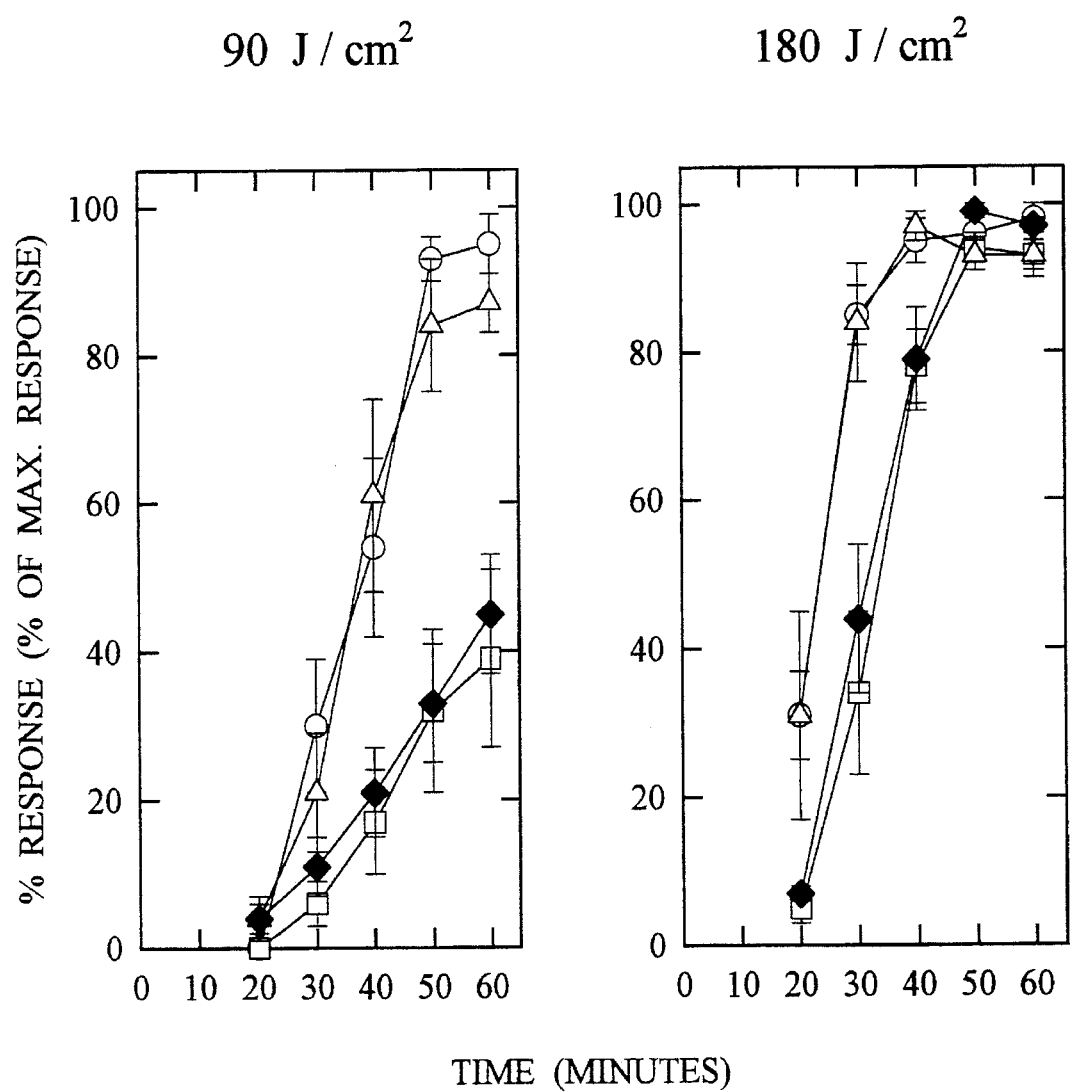

FIG. 11 is a plot showing the % Response curves (mean±SEM) for microphotolysis of rabbit (N=4) red blood cells that had been prepared in standard buffer with glucose and albumin (squares), buffer with glucose but not albumin (filled diamonds), buffer with albumin but not glucose (triangles), and buffer without albumin and glucose (circles).

Figure 12:
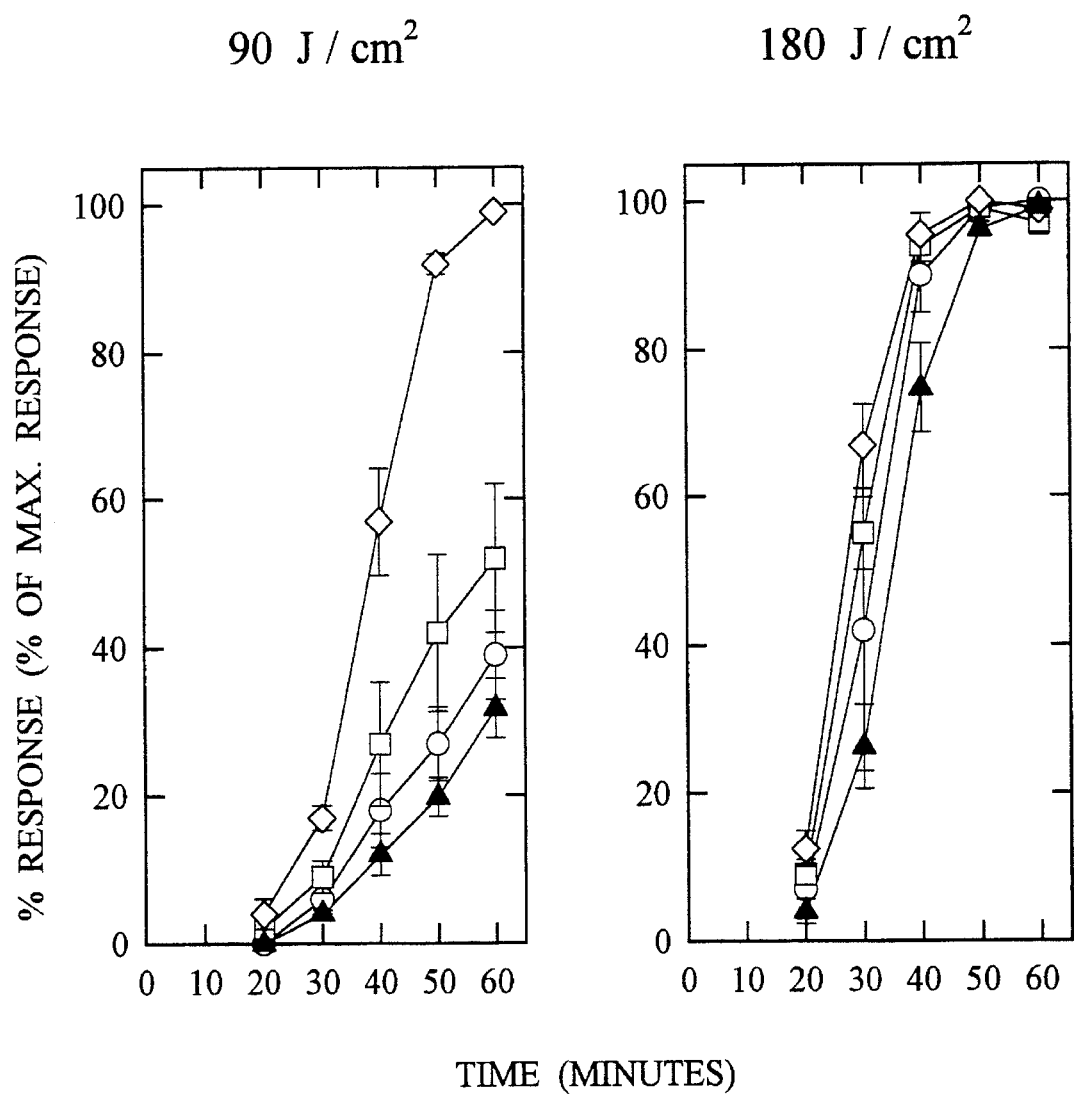

FIG. 12 is a plot showing the % Response curves (mean ±SEM) for microphotolysis of rabbit (N=6) red blood cells which had been previously incubated for one hour with diamide at a concentration of 5.0 milliMolar (diamonds), 0.5 mM (squares), 0.05 mM (circles), or 0.00 mM (filled triangles), with cell-attack stimuli of 180 J/cm$^2$ (right panel) and 90 J/cm$^2$ (left panel).

Figure 13:
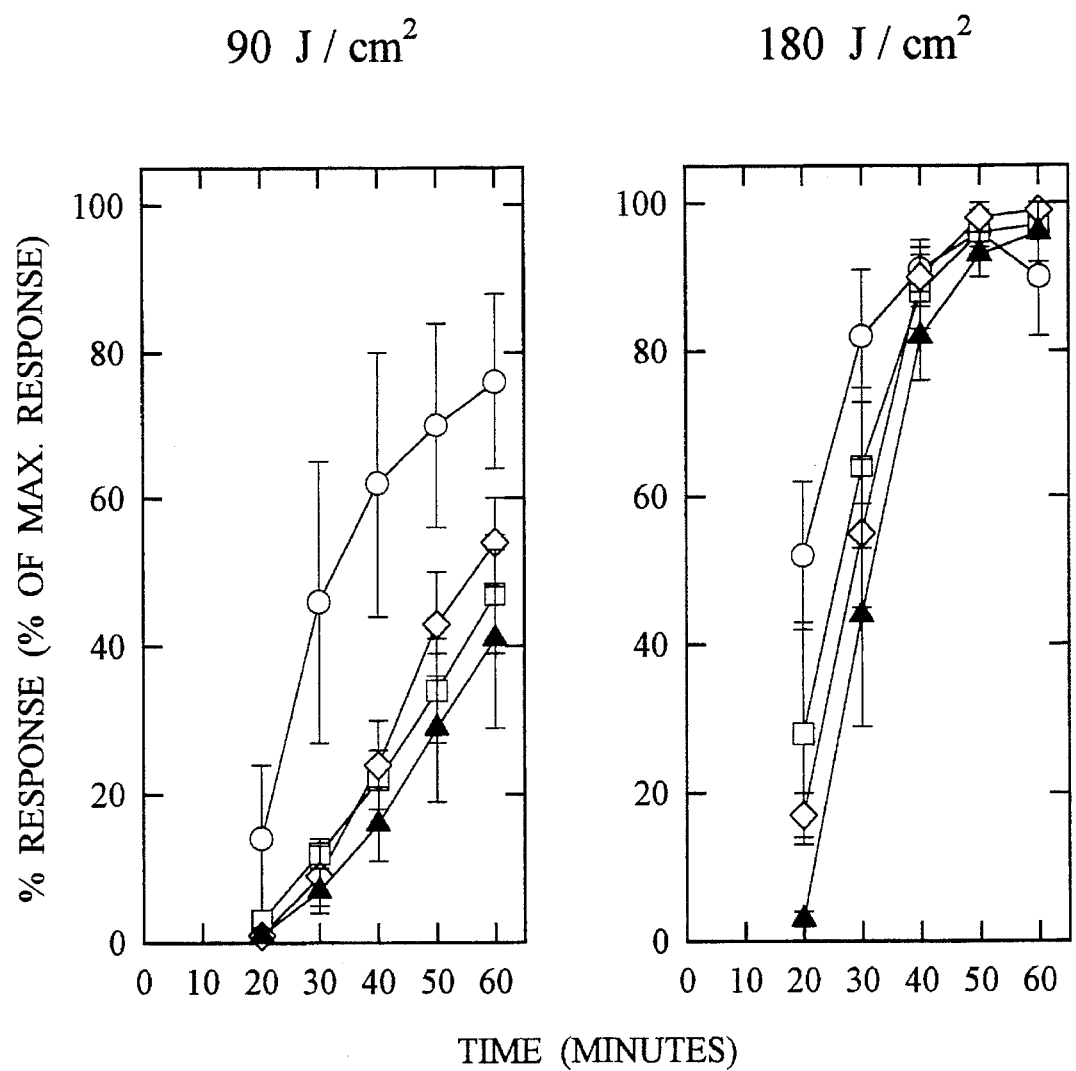

FIG. 13 is a plot showing the % Response curves (mean±SEM) for microphotolysis of rabbit (N=5) red blood cells which had been previously incubated for 20 minutes with Chlorpromazine at a concentration of 100 microMolar (circles), 30 μM (diamonds), 10 μM (squares), and 0 μM (filled triangles), with cell-attack stimuli of 180 J/cm$^2$ (right panel) and 90 J/cm$^2$ (left panel).

Figure 14:
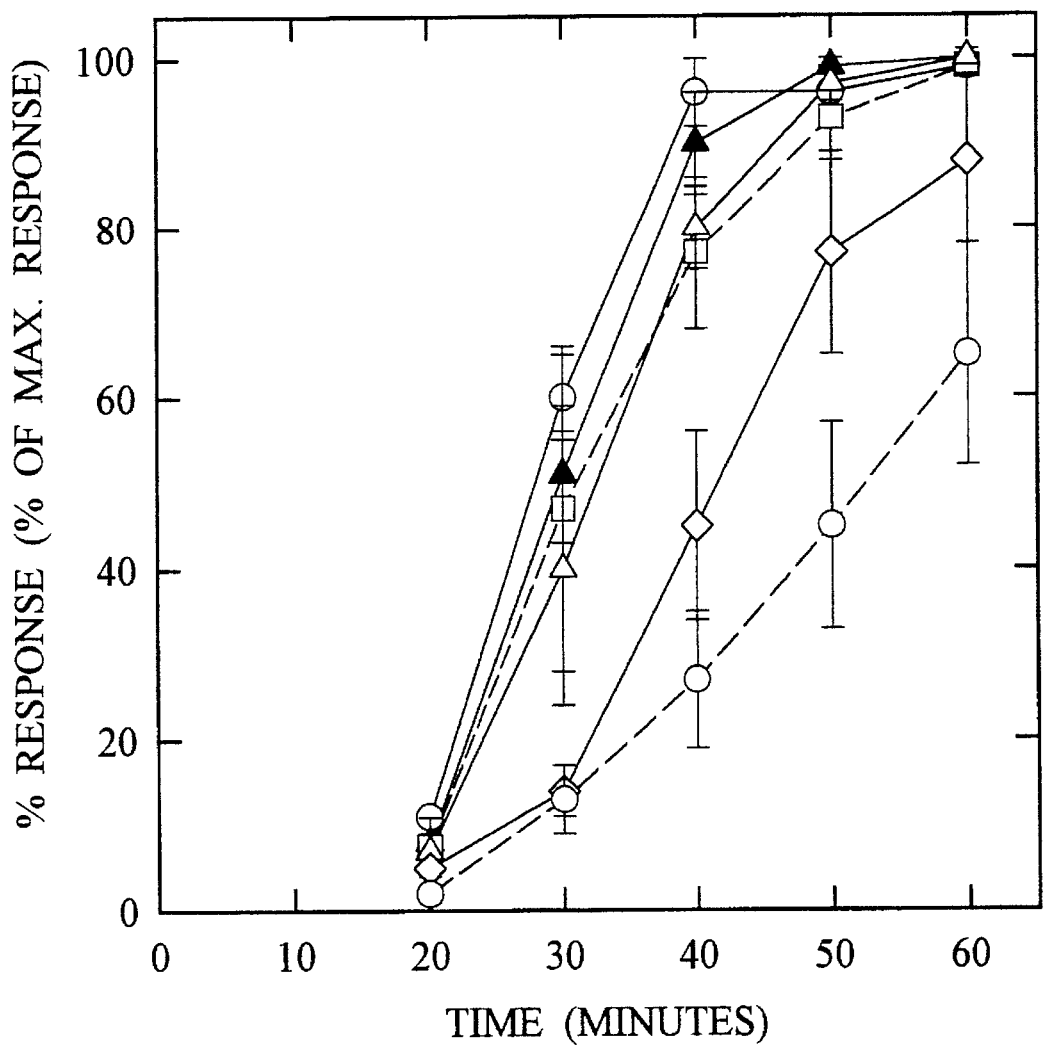

FIG. 14 is a plot showing the % Response curves (mean±SEM) for microphotolysis of rabbit (N=6) red blood cells which had been previously incubated for one hour with gluteraldehyde at a concentration of 0.02% (circles with dashed line), 0.01% (diamonds), 0.005% (triangles), 0.0025% (squares with dashed line), 0.00125% (circles), and 0.000% (filled triangles).

Figure 15:
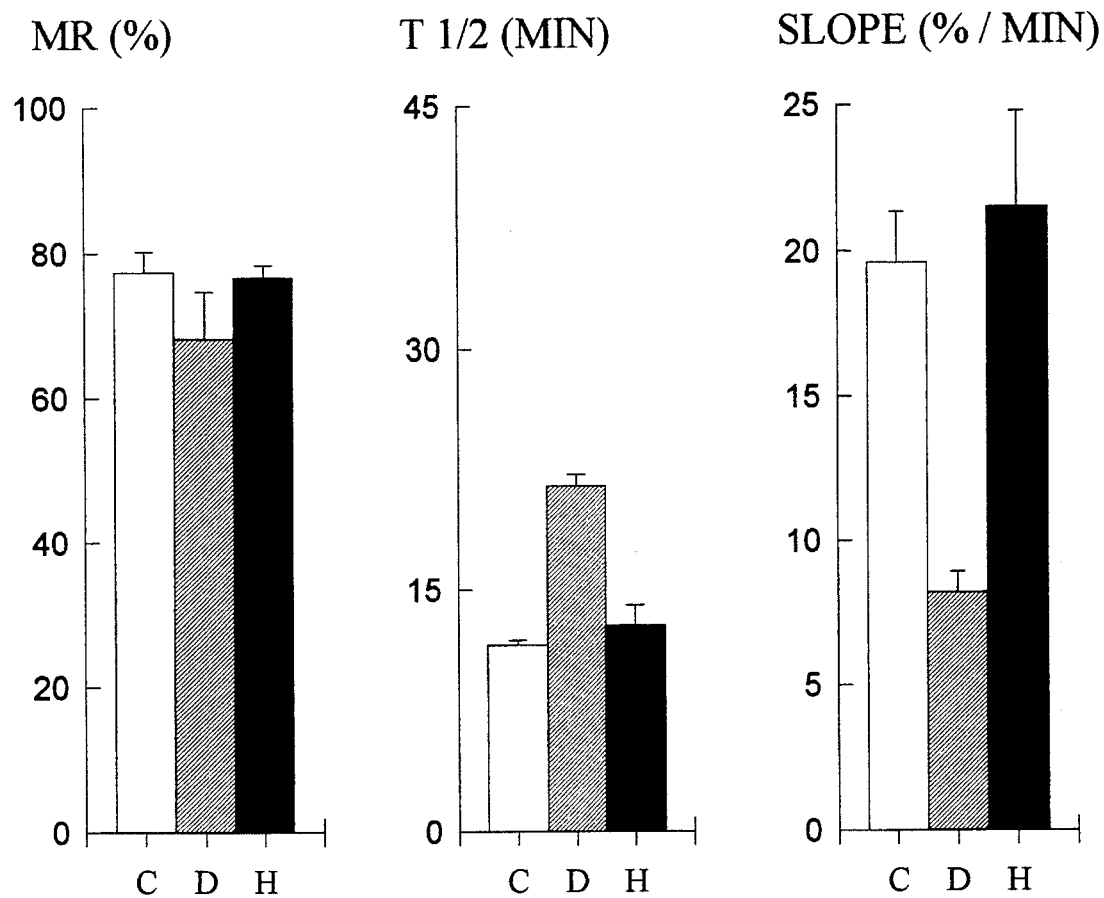

FIG. 15 is a bar graph showing the Percent Maximal Response (MR %) and the $T_{1/2}$ and Slope values of the % Response curves for microphotolysis of red blood cells from 5 normal control Sprague-Dawley laboratory rats (C) at 248±3.6 J/cm$^2$, 3 streptozoticin-induced insulin-dependent diabetic Sprague-Dawley rats (D) at 245±4.1 J/cm$^2$, and 6 diet-induced hypercholesterolemic Sprague-Dawley rats (H) at 249±2.7 J/cm$^2$.

Figure 16:
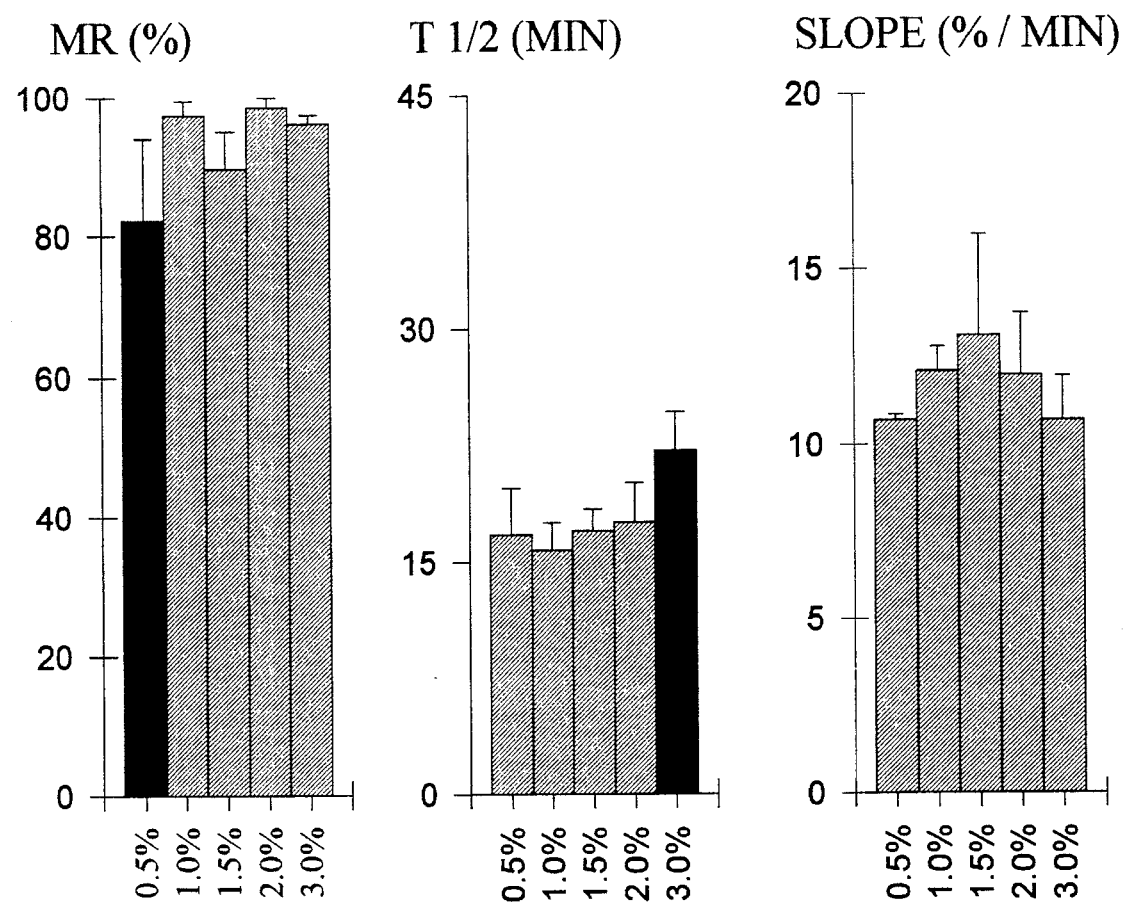

FIG. 16 is a bar graph showing the Percent Maximal Response (MR %) and the $T_{1/2}$ and Slope values of the % Response curves for microphotolysis of 0.5% to 3.0% concentrations of human (N=3) red blood cells. One subject received a cell-attack stimulus of 549±0.3 J/cm$^2$, the second subject received 340±1.1 J/cm$^2$, and the third subject received 198±1.3 J/cm$^2$ for all five cell concentrations.

Figure 17:
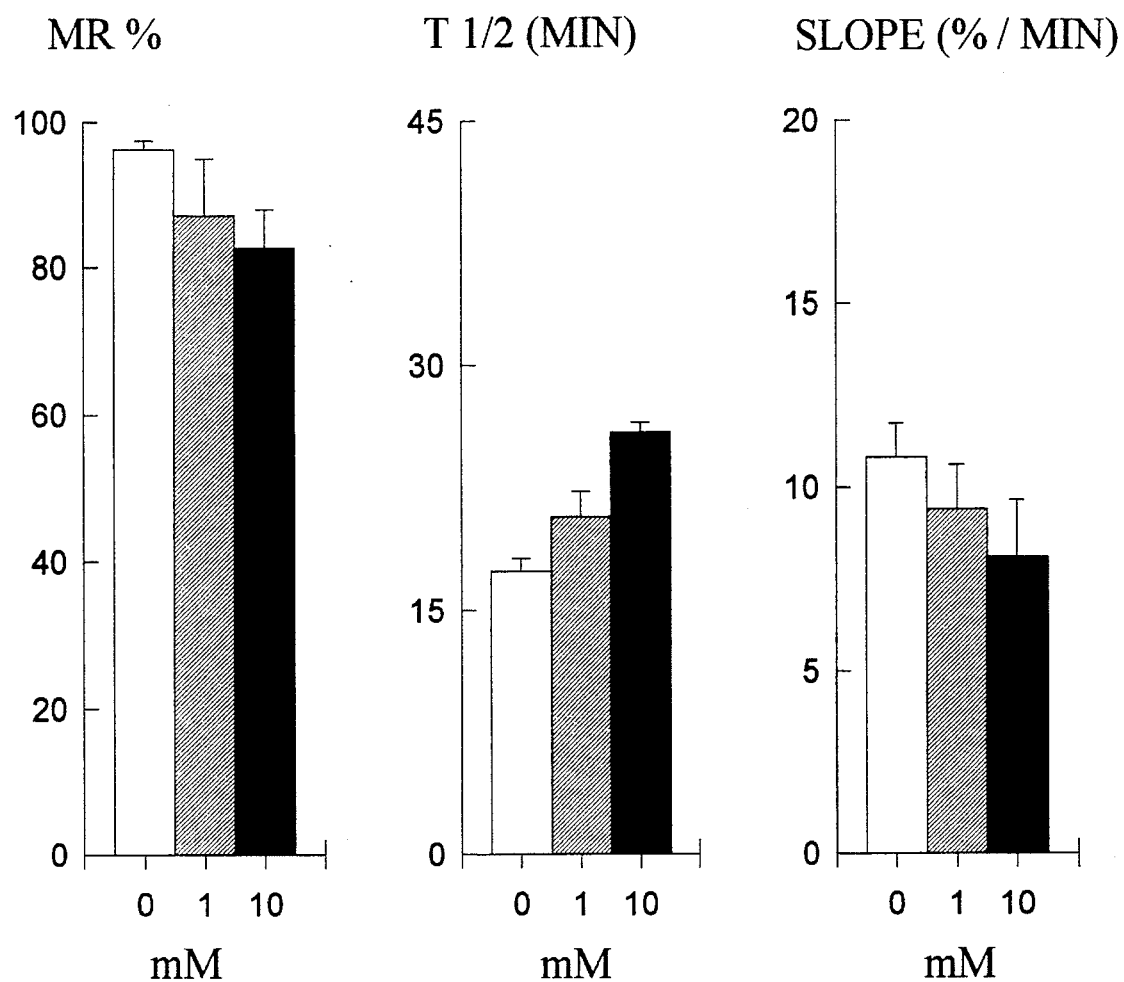

FIG. 17 is a bar graph showing the Percent Maximal Response (MR %) and the $T_{1/2}$ and Slope values of the % Response curves for microphotolysis of human (N=5) red blood cells which had been previously incubated at 4° C. FOR ONE HOUR with pentoxifylline (PTFX) concentrations of 10 milliMolar (filled bars), 1 mM (striped bars), and 0 mM (clear bars). One subject received a cell-attack stimulus of 658±6.6 J/cm$^2$, three subjects received 329±1.9 J/cm$^2$, and one subject received 196±0.7 J/cm$^2$ for all three pentoxifylline concentrations.

Figure 18:
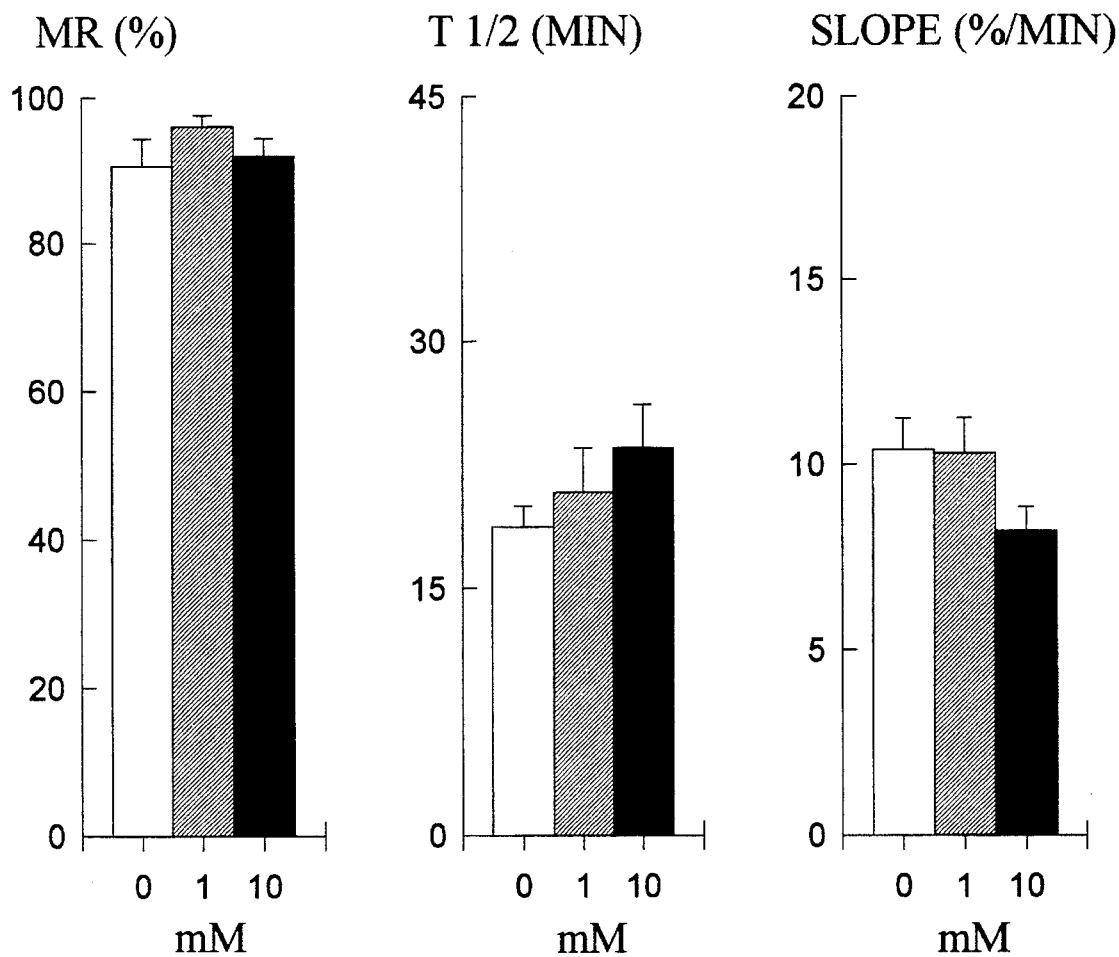

FIG. 18 is a bar graph showing the Percent Maximal Response (MR %) and the $T_{1/2}$ and Slope values of the % Response curves for microphotolysis of human (N=5) red blood cells which had been previously incubated at 4° C. FOR TWENTY-FOUR HOURS with pentoxifylline (PTFX) concentrations of 10 milliMolar (filled bars), 1 mM (striped bars), and 0 mM (clear bars). One subject received a cell-attack stimulus of 641±3.3 J/cm$^2$ three subjects received 330±1.7 J/cm$^2$, and one subject received 205±0.7 J/cm$^2$ for all three pentoxifylline concentrations.

Figure 19:
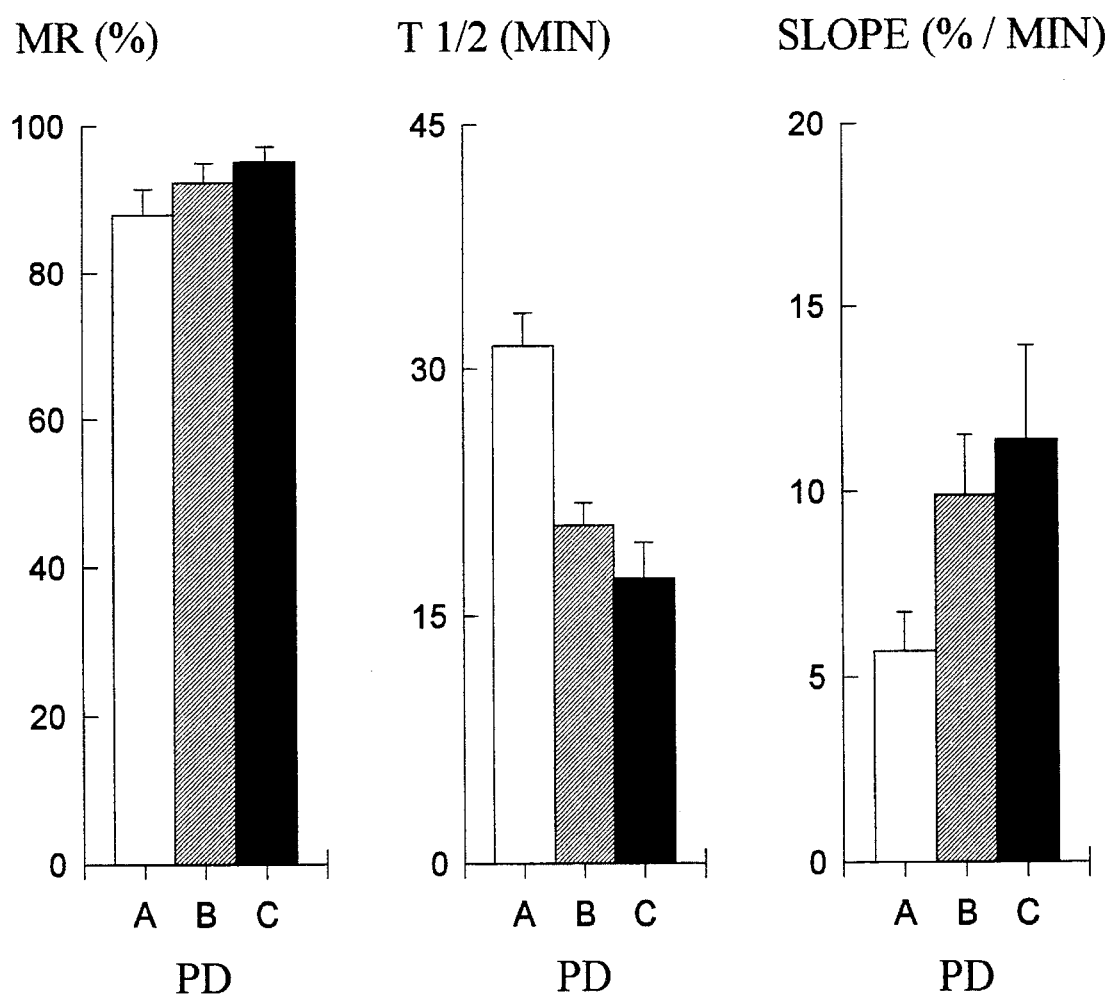

FIG. 19 is a bar graph showing the Percent Maximal Response (MR %) and the $T_{1/2}$ and Slope values of the % Response curves at cell-attack stimuli of A=243±2.9 J/cm$^2$ (clear bars), B=400±3.6 J/cm$^2$ (striped bars), and C=642±4.0 J/cm$^2$ (filled bars) for microphotolysis of red blood cells from four female and three male African-Americans who had no clinical indicators of sickle-cell disease.

Figure 20:
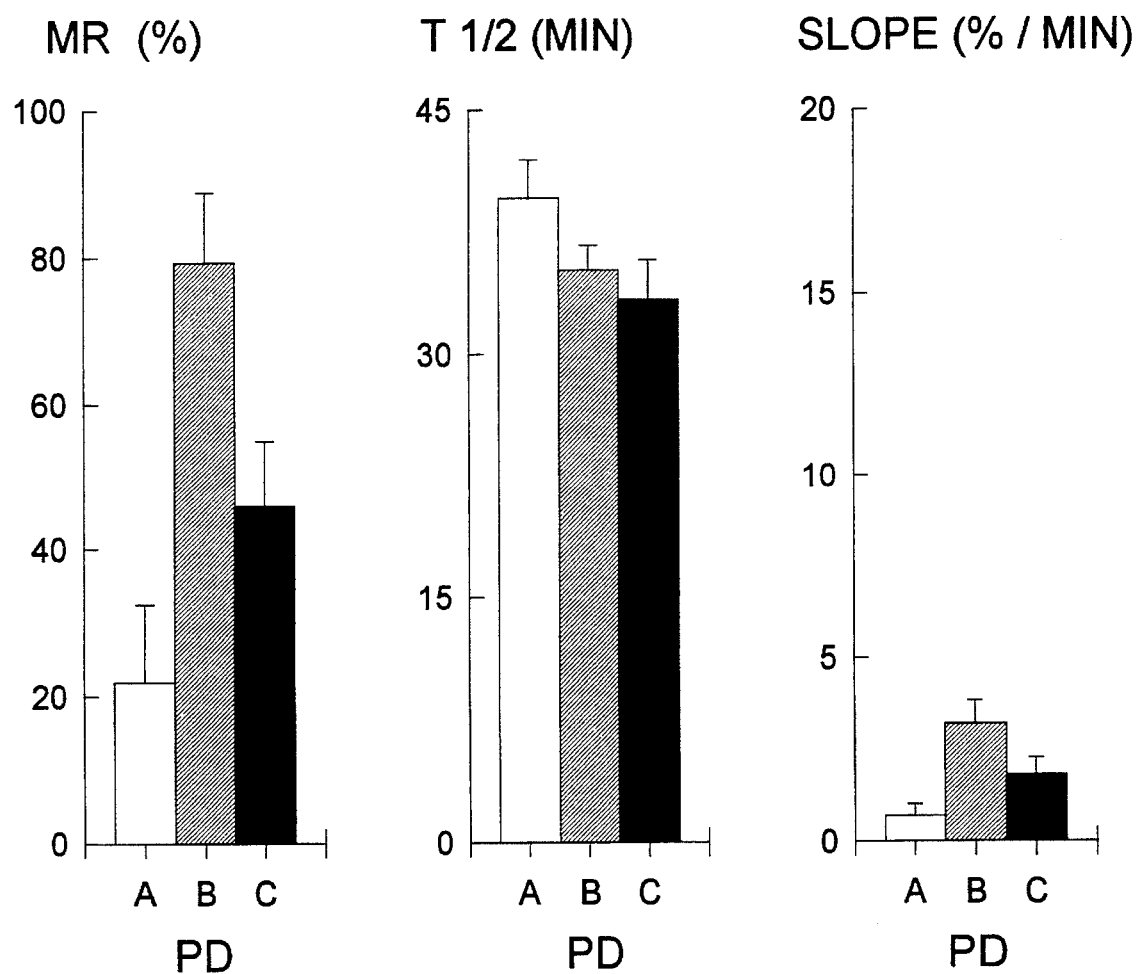

FIG. 20 is a bar graph showing the Percent Maximal Response (MR %) and the $T_{1/2}$ and Slope values of the % Response curves at cell-attack stimuli of A=247±1.1J/cm$^2$ (clear bars), B=395±5.5 J/cm$^2$ (striped bars), and C=643±4.0 J/cm$^2$ (filled bars) for microphotolysis of red blood cells from 2 female and 3 male African-Americans with clinical diagnosis of sickle-cell disease but not hemoglobin-F abnormality.

Figure 21:
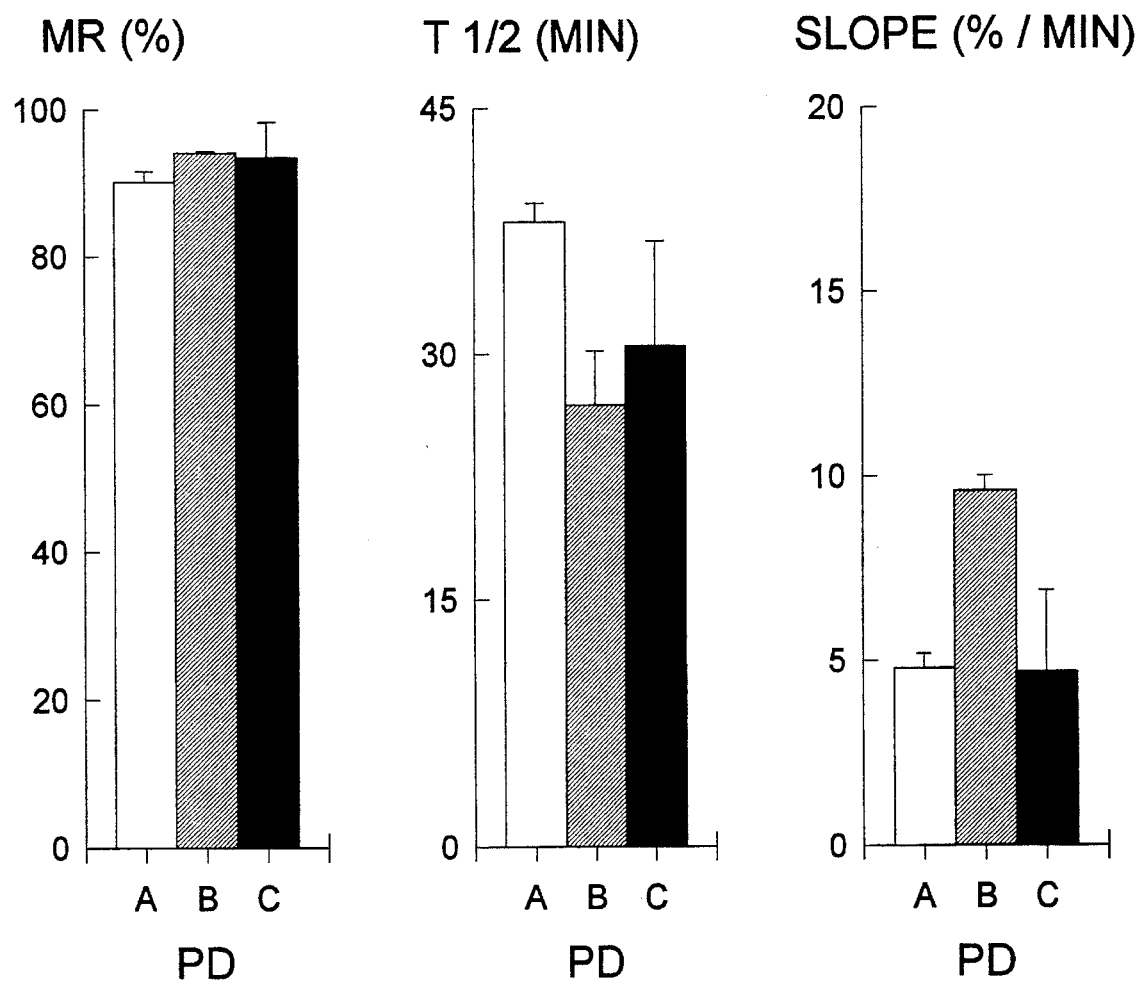

FIG. 21 is a bar graph showing the Percent Maximal Response (MR %) and the $T_{1/2}$ and Slope values of the % Response curves at cell-attack stimuli of A=253±2.8 J/cm$^2$ (clear bars), B=399±4.6 J/cm$^2$ (striped bars), and C=661±2.1 J/cm$^2$ (filled bars) for microphotolysis of red blood cells from 1 female and 1 male African-American with clinical diagnosis of sickle-cell disease and hemoglobin-F abnormality.

Figure 22:
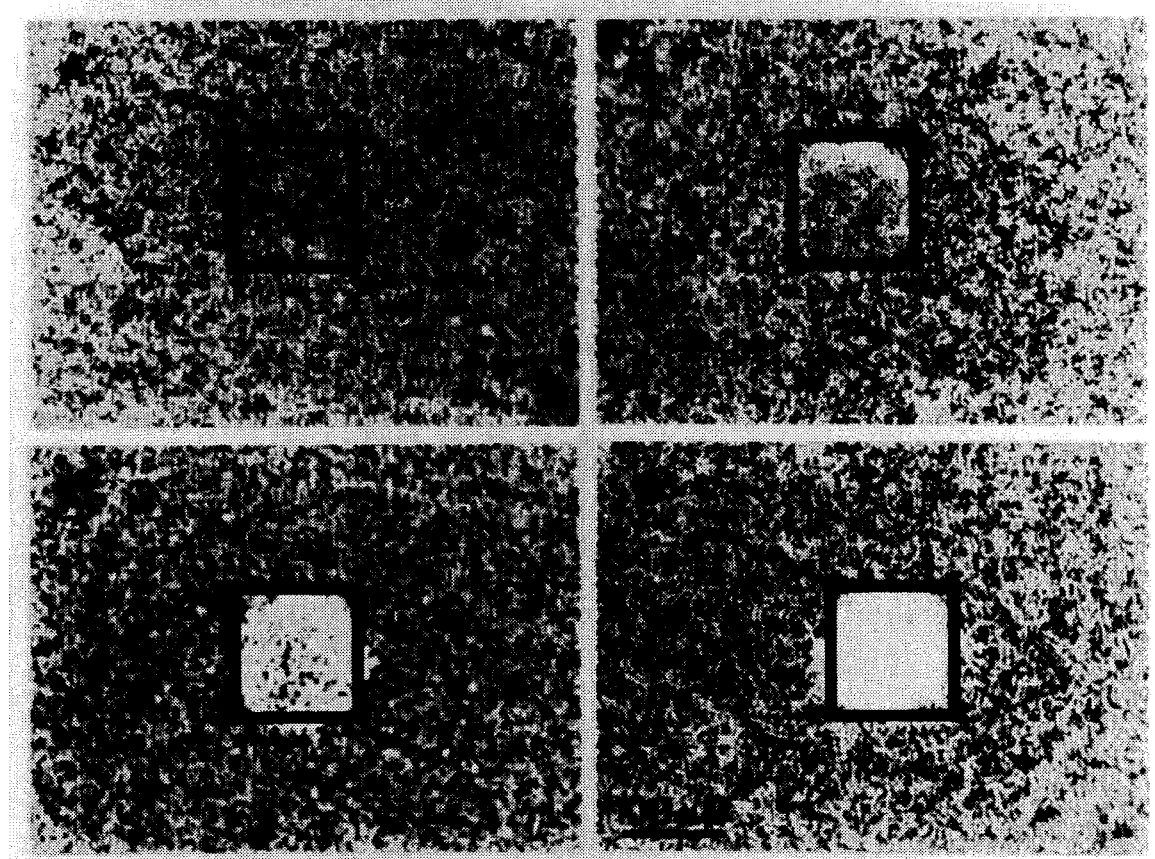

FIG. 22 is a photomicrograph showing the rectangular area of cell-attack for a cell micro-sample before activation as seen in the top left panel, 20 minutes after the start of activation as seen in the top right panel, 40 minutes after the start of activation as seen in the bottom left panel, and 60 minutes after the start of activation as seen in the bottom right panel.

DESCRIPTION OF THE PREFERRED EMBODIMENTS

Equipment Configuration

Although any light microscope having a 75–300 W arc lamp can be used in the present invention, a Zeiss model 20-T light microscope having a 100 W mercury arc lamp is utilized in the preferred embodiment for epi-illumination of the cell micro-sample through the microscope objective lens. A halogen lamp in the range of 50–300 W arc, preferably 100 W halogen is used for transillumination of the cell micro-sample through the microscope condenser. A television camera with external control of target voltage (a charged-coupled-device (CCD) or silicon-intensified-target (SIT) camera) is equipped with a microscope eye-piece attachment for adequate microscope-image capture, video-recording, video monitor display, and analysis of microphotolysis. A standard videocassette recorder, such as a (Panasonic model 6200), a time-date video-insertion generator such as a (Panasonic model 810), and moderate resolution television monitor (at least 600 horizontal lines preferred) is used to record the images of the microscopic area of the cell containing micro-sample for analyzing the images on-line or off-line at a convenient time.

The preferred embodiment of the present invention uses a light-microscopy objective lens (UMK 50X Leitz with 0.60 numerical aperture having a variable built-in lens diaphragm, a microscope tube factor of (1.25X), an X-Y coordinate movable microscope stage such as a Zeiss 20-T standard, and a brightfield substage condenser such as a Zeiss 20-T standard which are all ready available components. A microscope filter cube (Leitz model I-2 preferred) is utilized with a band-pass filter having a preferred range of (450–490 nm), a dichroic mirror preferrably 510 nm, and a long-pass barrier filter preferably 515 nm to match the excitation and emission frequencies of the chosen light-activated cell-attack fluorochrome such as (FITC) to measure the amount of electron deficient atoms released from the fluorochrome upon exposure to the excitation light frequency.

The epi-illumination light pathway through the microscope has provisions for a variable circular diaphragm, a fixed rectangular diaphragm (4.0×3.5 millimeter aperture preferred), and a neutral density filter carrier between the epi-illumination light source and the microscope filter cube to permit and control graded and known decreases in the amount of fluorochrome excitation light energy at the cell micro-sample on the microscope stage.

The transillumination light pathway through the cell micro-sample has provisions for a circular field diaphragm (22 mm diameter aperture preferred), a circular field light-limiter (7.5 mm diameter aperture preferred), and a color filter (green preferred for red blood cells) between the transillumination light source and the substage microscope condenser to permit control of background light energy at the cell micro-sample on the microscope stage.

Microscope Calibration Procedure

The present invention includes a new microscope light-calibration procedure to provide cell exposures to specific amounts of frequency-specific light energies which are quantitated as "light power density" multiplied by the "time of light exposure." In the following procedure, the critical steps are the independent adjustments of the epi-illumination and transillumination light pathways to give a specific light power from each pathway to a specific area at the cell micro-sample when the cell micro-sample is "in focus" on the microscope stage. Light power at any specific point in a light path can be measured by any of several instruments (such as an EGG model 580 radiometer). The preferred instrument is a model 61 United Technology (UT) Optometer which measures light power in the electrical power equivalents of milliwatts.

To begin calibration of the transillumination pathway, a glass microscope slide is covered with a glass coverslip and is positioned on the stage of the microscope. The epi-illumination pathway is blocked by closure of the variable circular diaphragm. After adjustment of the objective lens to bring the glass slide into focus on the microscope-attached television camera tube, the field diaphragm of the transillumination pathway is adjusted to a nearly closed position (a pin-hole opening) and the substage condenser is raised to bring the pin-hole opening of this field diaphragm into focus. The x-y adjustments of the substage condenser are then used to center the pin-hole opening of this field diaphragm in the microscope field-of-view.

The lamp power supply for the transillumination pathway is adjusted to approximately 9.2 volts. The light power is measured at the exit of the field diaphragm light-limiter, and the field diaphragm is opened until the light power at the exit of the light-limiter plateaus to give a value of 1.08 to 1.88 (1.48 preferred) milliwatts. If the plateau light power is too high or low at the light-limiter, the voltage of the lamp power supply should be adjusted. The light power is then measured at the glass slide on the microscope stage, and the built-in diaphragm of the substage condenser is partially closed to give 0.044 to 0.052 (0.048 preferred) milliwatts of transilluminated light power at the glass slide.

To begin calibration of the epi-illumination pathway, a drop of fluorescein diacetate (1.0 mg/ml concentration) is placed on a glass microscope slide and is covered with a glass coverslip. The slide is placed in a sample carrier which is positioned on the stage of the microscope. The transillumination pathway is blocked by placement of an opaque filter on the field limiter. The variable circular diaphragm of the epi-illumination pathway is slightly opened to focus a fluorescent image of a pin-hole in this diaphragm on the microscope-attached television camera tube. The diaphragm-holder adjustments are used to center the fluorescent image of this circular diaphragm in the television field-of-view.

The circular diaphragm is then opened fully and the fixed rectangular diaphragm is inserted into its carrier in the epi-illumination pathway. The holder adjustments for the rectangular diaphragm are adjusted to center the fluorescent image of this rectangular diaphragm in the television field-of-view. The bulb adjustments in the lamp housing for the epi-illumination pathway are then used to produce an even fluorescence across the television image of the rectangular diaphragm. The circular diaphragm of the epi-illumination pathway is closed completely and then opened to the point where the rectangular diaphragm is imaged as a uniform fluorescent rectangular area without any reflections of stray light rays in the television field-of-view.

The light power of the epi-illumination pathway is measured at the focal plane of the objective lens (which corresponds to the position of the coverslip in the sample carrier on the microscope stage when that coverslip is in focus in the television field-of-view), and is adjusted to a value of 0.39 to 0.41 (0.40 preferred) milliwatts by partial closure of the diaphragm in the objective lens. (If the light power is too low at this point, the epi-illumination light bulb has aged and should be replaced.)

Neutral Density (ND) filters are then placed one at a time in the epi-illumination pathway to provide calibration of graduated decreases in epi-light power at the focal plane of the objective lens. Nominal epi-light power values are 0.30–0.32 milliwatts for an ND of 0.1, 0.18–0.20 milliwatts for an ND of 0.3, and 0.10–0.12 milliwatts for an ND of 0.6.

The amount of epi-illumination, which is used to provide a light-stimulated attack to disrupt cells in a micro-sample (described below) on the microscope stage, is quantitated as a light energy density (ED) which equals epi-light power at the micro-sample, multiplied by time of epi-light exposure, divided by the micro-sample area of epi-light exposure. For the above-described equipment configuration and calibration procedure, the area of epi-light exposure is determined by the fixed rectangular diaphragm which has a projected image area of 0.000175 cm$^2$ (140.91 μm×124.24 μm) at the focal point of the microscope objective lens.

A common unit for light energy density is Joules/cm$^2$ where one Joule equals the total energy that is released in one second by a one-ampere current flowing through a one-ohm resistor (which is electrically equivalent to one watt or 1000 milliwatts of power for one second). For the above-described calibration procedure, the epi-light power is measured as milliwatts (mw) by the UT Optometer, and epi-exposure time is measured in 0.01 minute increments by the time-date video-insertion generator. The following formula is used to convert these measured units into epi-light energy density (ED) with units of J/cm$^2$ (i.e. Joules÷cm$^2$):

Light Energy Density=Light Power×time÷area;

or

Joules/cm$^2$=Watts×Seconds×cm$^2$;

or

ED (J/cm$^2$)=(mw÷1000)×(minutes×60)÷(0.000175 cm$^2$);

or

ED (J/cm$^2$)=(342.86)×(mw)×(minutes)÷1 cm$^2$.

The above-described calibration procedure gives the following epi-light energy densities (ED at the focal point of the microscope objective lens) which result from use of the preferred epi-illumination neutral density (ND) filters:

| ND | POWER (mw) | ED (Joules/cm$^2$) |
|---|---|---|
| 0.0 | 0.40 | 137.14 × exposure mins |
| 0.1 | 0.32 | 109.71 × exposure mins |
| 0.3 | 0.20 | 68.57 × exposure mins |
| 0.6 | 0.10 | 34.29 × exposure mins |

Typical exposure times are 2 to 10 minutes to give final gradations in the epi-light energy density over a range of 68.58 to 1,371.40 J/cm$^2$ for light-stimulated attack to disrupt cells in a micro-sample on the microscope stage.

The last step in microscope calibration is adjustment of the camera target-voltage when the cell micro-sample is first placed on the microscope stage. This adjustment qualitatively positions the camera target-voltage (baseline target current) at approximately the midpoint of the linear voltage range to give a reasonable television picture for the transilluminated-light image of the cell micro-sample. Quantitative measurement of this starting camera voltage is not required because subsequent changes in light-intensity at the camera target are measured as a percentage change in camera target current, which is independent of the starting target voltage when that target voltage is in the linear voltage range of the camera.

Cell Collection Procedure

Arterial, venous, or mixed capillary (finger stick) blood can be used for microphotolysis of red blood cells. The data in this patent report were obtained from standard venipuncture of the antecubital vein in awake humans and the ear vein of awake New Zealand white rabbits (2.5–4 kg) to collect blood (typically 1–2 ml) into sterile tubes which contained citrate to prevent clotting.

Blood is stored in a 0°–4° C. refrigerator before preparation of blood specimens and cell micro-samples. All cell and solution procedures use only sterile disposable pipette tips, microcentrifuge tubes, bottles, stoppers, and labware to prevent cell contamination and infection.

Buffer Solution Preparation

Subsequent blood dilutions (described below) are done with a typical buffer solution consisting of 7.6 g/l NaCl, 0.26 g/l $NaHPO_4 \cdot H_2O$, 1.28 g/l $Na_2HPO_4$, 4 g/l glucose, and 5 g/l bovine serum albumin. Buffer solution pH is adjusted to 7.4 (normal blood pH) by addition of 1N NaOH. The final osmolality of this buffer solution is 311 mOsm (near normal blood pH). Other buffer solutions can be used; however, glucose and albumin are necessary ingredients to stabilize the cell preparation and to provide restricted-permeability molecules for control of transcellular water movements which can affect the subsequent microphotolysis process. Likewise, a final osmolality of 295–315 mOsm is critical since overall buffer solution osmolality also affects the rapid phase of transcellular water movements.

The final step in buffer solution preparation is vacuum aspiration of the buffer solution through a sterile 0.2 micron Nalgene filter to remove any bacteria or other particulate contaminants. The filtered buffer solution is allocated into sterile glass bottles (20 ml preferred) with rubber stoppers for subsequent cell-specimen preparation.

Fluorochrome Solution Preparation

The type of light-activated agent that is used for cell attack is specific to the type of cell to be analyzed, and there is more than one type of cell-attack agent for any one cell type. For example, phloxine B, eosin-isothiocyanate, pheophorbide, and protoporphyrin have previously been used for photohemolysis in a relatively large-volume cuvette. The preferred cell-attack fluorochrome for damage of red blood cell membranes by microphotolysis is fluorescein isothiocyanate (FITC) which is conjugated to a larger macromolecule (20,000 dalton dextran preferred). FITC-dextran is preferred because it does not enter the cell, and there is little blood absorption of light energy at the FITC-excitation frequency of 480 nanometers. Thus, the measured light energy which is projected onto the micro-sample gives a precise amount of activated FITC as a cell-attack agent.

The FITC-dextran is mixed with a 0.9% NaCl solution to give an FITC-dextran concentration of 50 mg/ml. In the subsequent cell micro-sample, the final FITC-dextran concentration in the micro-sample should be in the 2–8 mg/ml range to give the best light-activated cell-attack stimulus for microphotolysis of red blood cells.

Cell Specimen Preparation

Microphotolysis can be applied to different types of cells, and the cell-separation part of the cell preparation procedure will depend on the cell type. The following describes the procedure for red blood cells.

The refrigerated blood is inverted gently to mix the blood, and is then diluted (1 to 1) with equal parts of the buffer solution. A small amount (80 to 100 μl) of the diluted blood is drawn into a microhematocrit tube which is spun in an IEC MB hematocrit centrifuge at the recommended speed to compact the red blood cells toward one end of the microhematocrit tube. The length of the compacted red blood cells is then measured to give the hematocrit (% cells) of the diluted blood.

The final cell-specimen is a combination of the diluted blood, FITC-dextran, a test drug (if any), and the buffer solution to give a cell-specimen volume of 1 ml with a composition of 0.5 to 6.0% red blood cells, 2.0 to 8.0 mg/ml FITC-dextran, 0 to 10 mg/ml of test drug, and the remainder as buffer. As an illustration, a cell specimen with 4 mg/ml of FITC-dextran (which comes as a 50 mg/ml fluorochrome solution as described above), 3% red blood cells (which comes from a diluted blood solution with 25% hematocrit), and 3 mg/ml of test drug (which comes as a 20 mg/ml solution) is obtained by mixing 0.08 ml (calculated as 4/50) of the fluorochrome solution, 0.12 ml (calculated as 3/25) of the diluted blood, 0.15 ml (calculated as 3/20) of the test drug solution, and 0.65 ml (calculated as 1.0–0.08–0.12–0.15) of the buffer solution. Based on this approach, individual, or combinations of, soluble materials or drugs can be tested for an effect on cell response to microphotolysis by standardized light-activated cell-attack stimuli.

Cell Micro-Sample Preparation

Any type of small volume (50 μl or less) chamber of transparent water-impervious material, such as plastic or glass, can be used to give a cell micro-sample on the microscope stage. The crucial aspect is a chamber and filling procedure that prevents micro-sample loss of water (which would change the cell micro-sample constituent concentrations to alter the microphotolysis). The following describes a simple new micro-sample preparation.

A hemacytometer (Neubauer preferred) and cover slip are sterilized in alcohol and air-dried. As a novel approach of the present invention, four Kerr absorbent points (dental cotton sticks for cavity preparations) are placed in a 0.9% NaCl solution to saturate them. A fine forceps is then used to place two saturated Kerr points in each side-well of the hemacytometer, with care to ensure that no Kerr point touches the inside edge of the hemacytometer trough (otherwise, the solution in the Kerr points would dilute the micro-sample constituent concentrations). The saturated Kerr points are a novel approach to provide a "saturated" water vapor pressure to "replace" any potential loss of micro-sample water by evaporation through the entrance of the hemacytometer chamber to the atmosphere.

A small drop-dispenser is used to pick up a solution of 2.5 g/l globulin (made in distilled water), and this solution is applied to coat the coverslip rests of the hemacytometer. The coverslip is placed on the hemacytometer rests and is lightly tapped to seal the coverslip to the globulin-coated hemacytometer rests. This is a novel approach of the present invention to reduce evaporation of water from the cell micro-sample. In the customary approach, the coverslip just lays on the hemacytometer rests without use of a sealant. Small irregularities in the "rests" leave small openings between the coverslip and the "rests." The use of a globulin solution in the present invention to seal these small openings is a novel approach to prevent evaporative water loss from the cell micro-sample.

The cell micro-sample solution is gently mixed by inversion of the solution vial. A sterile transfer pipette is used to aspirate the cell micro-sample solution from the vial and to apply 22–25 μl of the solution to the opening of the hemacytometer/coverslip chamber. Capillary action draws the cell micro-sample solution into the hemacytometer chamber (which has a preferred depth of 0.1 mm to standardize the number of cell layers).

The hemacytometer is then placed in a sample carrier which is positioned on the microscope stage. At this point, the transillumination light pathway is opened (by removing the opaque filter from the field limiter) and the cell micro-sample is brought into focus. The television camera target-voltage is adjusted to the midrange (described above in the microscope calibration procedure).

Microphotolysis Cell-Attack Procedure

The television-microscope images in the following procedure are video recorded for post-procedure analysis. (These images can also be analyzed on-line at the time of the procedure.)

A five-minute waiting period is used for cells to settle in the micro-sample hemacytometer chamber. Room temperature is recorded and hemacytometer temperature is kept at 23.5° to 24.5° C. to minimize Brownian motion of the red blood cells in the cell micro-sample. The cells are brought to focus during transillumination to give a control reading of "background optical density" for the cell micro-sample. Then, the transillumination pathway is closed by placing the opaque filter on the field limiter.

The time-date video-insertion generator is reset to 0.00 time (in minutes) and is started at the instant that the epi-illumination light pathway is opened (by removing an opaque filter from the epi-light pathway). The focus of the fluorescent image is checked and readjusted if necessary. The epi-illumination is left on for the necessary time (1 to 6 minutes preferred) with a preselected neutral density filter in the epi-light pathway to give a desired cell-attack stimulus which is measured as an epi-illumination energy density in Joules/cm$^2$ (as described above in the microscope calibration procedure). At the end of the cell-attack stimulus time, the epi-illumination pathway is closed (by placing the opaque filter in the epi-light pathway), and the transillumination pathway is opened (by removing the opaque filter on the field limiter) to give cell micro-sample images. These cell images are recorded until lysis (disruption of cells) has reached a maximum (less than 5 intact cells remaining in the rectangular epi-illumination area) or 60 minutes has elapsed, whichever occurs first.

At this point, the hemacytometer cell micro-sample is repositioned manually on the microscope stage to give another micro-sample area for application of a second cell-attack stimulus. This procedure allows many measurements of microphotolysis at different cell-attack levels (epi-illumination energy densities) on each cell micro-sample. Hemacytometer grid etchings are used to identify the location of each cell-attack area which prevents inadvertent overlap of cell-attack areas in multiple microphotolysis procedures on the same cell micro-sample.

Microphotoanalysis Procedure

After the cell micro-sample (in the hemacytometer) has been placed on the microscope stage, there is a five-minute period for cells to settle in the micro-sample chamber. At this point, transillumination gives a relatively dark speckled-image of the micro-sample in the television field of view. The speckled nature of this image is caused by the presence of red blood cells with a biconcave shape, as shown in FIG. 22.

This transillumination speckled-image area (which is 6 to 10 times larger than the epi-illumination rectangular diaphragm area) is digitized (Image Technology digitizing board preferred) to give a digital image with 512×512 pixels (1024×1024 would increase analysis precision) with a digital value between 0 and 255 to represent the light intensity of each image pixel. The mean of ALL pixel values in this speckled image is calculated as a micro-sample "background light intensity (BLI)" with a value between 0 and 255 (a typical value is 100 to 150).

As described above (section on Microphotolysis Cell-Attack Procedure), the epi-illumination light pathway is opened (by removal of the opaque filter) for a pre-selected time to activate a cell-attack stimulus within the epi-illumination rectangular area on the cell micro-sample image. Then, the epi-illumination light pathway is closed. Transilluminated micro-sample images are then digitized at 30-second intervals over the next 60 minutes (or until there are 5 or fewer intact cells within the rectangular cell-attack area in the image).

After exposure to the epi-illumination rectangular area of cell-attack stimulus, the part of the cell micro-sample that was exposed becomes brighter and loses its speckled appearance as a function of time in the transilluminated image. This occurs because cells in the cell-attack area lose part or all of their contents and their membranes lose functional integrity as a microphotolysis response to the cell-attack stimulus.

The values of the image pixels in the rectangular (approximately 60×50 pixels) cell-attack area are averaged, and this pixel average is compared in successive digitized images for 60 minutes or until this pixel average rises to a plateau value which does not change by more than ±1% for 3 minutes (6 images). The transillumination image at 60 minutes or the first transillumination micro-sample image with a plateau for the average value of the image pixels in the rectangular cell-attack area is defined as the maximal cell-response image. The 30 highest pixel values (10% of total pixels) in the rectangular cell-attack area of the maximal cell-response image are averaged to define a digital value which represents an image area with no intact cells (called the "total-lysis" light intensity or TLI).

The average value for all pixels in the rectangular cell-attack area is defined as a "Response-Area Light Intensity (t)" for each digitized transilluminated micro-sample image. These Response-Area Light Intensities (RLI(t)) are converted to relative Response-Area Optical Densities (Response OD(t)) by the following formula:

$$\text{Response OD}(t) = 100 \, (TLI-RLI \, (t))/(TLI-BLI),$$

where TLI is the total-lysis light intensity in the cell-attack area of the transilluminated micro-sample image, BLI is the background light intensity for the entire transilluminated micro-sample image, and RLI(t) is the response light intensity as a function of time in the cell-attack area of the transilluminated micro-sample image. The quantity (TLI–BLI) represents the range of the average light intensity for the entire transilluminated micro-sample image. The zero-time average light intensity of the rectangular area before cell-attack (RLI(0)) can be larger or smaller than the average background light intensity (BLI) for the entire transilluminated micro-sample area. Thus, the zero-time Response-Area OD(0) can be larger or smaller than 100% of the optical density range for the entire transilluminated micro-sample area. The average Response-Area Light Intensity in the maximal cell-response image (RLI plateau) can be smaller than the total-lysis light intensity (TLI) because some intact cells can remain in the rectangular area of the maximal response image. Thus, the minimum plateau Response-Area OD can be larger than zero.

FIGS. 1 and 2 show the Response-Area optical densities as a function of time from the beginning of a five-minute exposure of human red blood cells to three levels of cell-attack stimuli (expressed as Joules per centimeter squared). A cell-attack stimulus of 245 J/cm$^2$ gives a Response-Area OD which decreases from a zero-time value of 105% to a minimum plateau value of 18% at 46 minutes after the beginning of the cell-attack exposure (FIG. 1). A larger cell-attack stimulus of 401J/cm$^2$ gives a Response-Area OD which decreases from 102% to 6% at 31 minutes after the beginning of cell-attack (FIG. 1), while an even larger cell-attack stimulus of 638 J/cm$^2$ gives a Response-Area OD which decreases from a zero-time value of 91% to a minimum plateau value of 3% at 37 minutes after the beginning of cell-attack (FIG. 2). These data show that changes in cell-attack stimulus alter the time-dependent Response-Area OD curve by affecting the magnitude of the maximal OD change, the slope of the Response-Area OD curve, and the time to the half-maximal change in Response-Area OD.

The variation in zero-time Response-Area OD occurs before application of the cell-attack stimulus and adds statistical variation to the time-dependent Response-Area OD curve that is produced by the cell-attack stimulus. To remove the effect of this attack-unrelated variation in zero-time Response-Area OD, the following three-step normalization procedure is performed as illustrated in FIG. 3, wherein:

1) The Maximal Microphotolysis Response (MR) is calculated as the zero-time Response-Area OD (ZROD) minus the Minimum Plateau Response-Area OD (PROD); i.e. MR=ZROD–PROD.

2) The Percent Maximal Response (MR %) is calculated as 100 times the Maximal Microphotolysis Response (MR) divided by the zero-time Response-Area OD (ZROD); i.e. MR %=(100)(MR)/(ZROD).

3) The % Response at a specific time t (% Response (t)) is defined as 100 times the quantity, zero-time Response-Area OD (ZROD) minus the Response-Area OD at time t (ROD(t)), that resultant quantity divided by the Maximal Microphotolysis Response (MR); i.e. % Response (t)=(100)(ZROD-ROD(t))/MR.

The Percent Maximal Response (MR %) is a measure of the percentage number of cells which are eventually disrupted in the rectangular area that was exposed to the cell-attack stimulus. The Response (t) is a measure of the number of cells which have been disrupted as of time t in the rectangular area that was exposed to the cell-attack stimulus, and is expressed as a percentage of the eventually disrupted number of cells.

As shown in FIG. 4, the three % Response curves are generated by application of the above formulas to the three Response-Area Optical Density curves in FIGS. 1 and 2. The above-described normalization procedure produces time-dependent % Response curves which change from 0% to 100% after the beginning of the cell-attack stimulus, irrespective of the variation in the zero-time Response-Area OD (ZROD in FIG. 3). These normalized data show that changes in cell-attack stimulus alter the time-dependent % Response curves by changing the maximum slope and the time to the half-maximal (50%) value of the curve.

Moreover, FIG. 5 repeats the % Response curve (open circles) of FIG. 4 for the 245 Joules/cm$^2$ cell-attack stimulus to quantitate precise changes in cell response to specific levels of cell-attack stimuli by defining:

1) the response half-time ($T_{1/2}$) as the period from the beginning of cell-attack to the time of the 50-percent response value, and 2) the largest slope of the % Response curve as the Slope at time t=$T_{1/2}$.

$T_{1/2}$ is a measure of average cell resistance to disruption by the cell-attack stimulus. The largest slope is a measure of the fastest rate of cell disruption at any time after the beginning of the cell-attack stimulus. This slope provides an index of the "population variation" in individual cell resistance to disruption by the cell-attack stimulus. For example, a population of homogeneous cells, each with exactly the same cell-resistance to disruption, would give a "step" % Response curve with a zero-value until time equal to $T_{1/2}$, and a 100% value after time equal to $T_{1/2}$. In contrast, a very heterogeneous population of cells, some with very low resistance and some with very high resistance and some throughout the range from very low to very high resistance to disruption, would give a % Response curve with a shallow slope beginning shortly after the beginning of the cell-attack stimulus and reaching a 100% value at a time much after the $T_{1/2}$ value.

The Slope of the % Response curve at time equal to $T_{1/2}$ can be obtained in several ways. For example, the value of the first derivative of a polynomial curve-fit to the % Response curve at time equal $T_{1/2+ee}$ would give the slope value of the % Response curve at time equal to $T_{+e,fra\ 1/2}$. The following gives a simple method for calculation of the Slope of the % Response curve at time equal to $T_{1/2}$:

1) T70 is defined as the period (in minutes) from the beginning of cell-attack to the time when the % Response equals 70%.

2) T30 is defined as the period (in minutes) from the beginning of cell-attack to the time when the % Response equals 30%.

3) Slope at $T_{1/2}$ is defined as 70% minus 30%, that quantity divided by the quantity, T70 minus T30, with units of % Change in Response per Minute (abbreviated as %/MIN); i.e. Slope at $T_{1/2}$ (% /MIN)=(70–30)/(T70–T30).

This simple method is reasonably accurate because all % Response curves range from 0% to 100% in ordinate value, and all Response curves are approximately linear in the 30% to 70% response range such as one in FIG. 5 for example.

Microphotolysis of Animal Cells

FIG. 6 shows the % Response curves (mean+SEM) on day 1 at 7 hours (circles), day 2 (squares), day 3 (triangles), day 4 (diamonds), and day 5 (inverted triangles) after blood collection for red blood cells from four rabbits with micro-sample composition of 4% red blood cell concentration and 2 mg/ml FITC-dextran (150,000 daltons). The cell-attack stimulus was 210 J/cm$^2$ for all curves. The % Response curves are identical to each other when microphotolysis is conducted on cell micro-samples from 7 hours to 5 days after blood collection from rabbits. The % Response curve changes by a progressive shift to the left when microphotolysis is conducted on cell micro-samples during the first 6 hours after blood collection from rabbits.

FIG. 7 shows % Response curves (mean±SEM) for the effect of cell-attack stimuli of 105 Joules/cm$^2$ (open squares), 126 Joules/cm$^2$ (filled squares), 159 Joules/cm$^2$ (open triangles), 168 J/cm$^2$ (filled triangles), 210 J/cm$^2$ (open diamonds), and 210 J/cm$^2$ (filled diamonds) on rabbit (N=3) red blood cells with micro-sample composition of 4% hematocrit and 2 mg/ml FITC-dextran (150,000 daltons). The cell-attack stimuli for the open symbols were achieved by lower epi-illumination light power densities for 10 minutes of epi-light exposure, while the cell-attack stimuli for the filled symbols were achieved by higher epi-illumination light power densities for 8 minutes of epi-light exposure. The % Response curve for a lower epi-illumination light power at a longer epi-illumination exposure time (open symbols) is the same as that for a higher light power at a shorter exposure time (filled symbols) when these give the same energy densities as equivalent cell-attack stimuli. This observation remains true for any energy density, provided that the exposure time is at least 4 minutes in duration. FIG. 7 also demonstrates that the Slope and $T_{1/2}$ values of the % Response curves are different for different levels of cell-attack stimuli. The % Response curves for rabbit red blood cells are also different for different micro-sample concentrations of FITC-dextran when the FITC-dextran concentration is below a critical value of 2.0 mg/ml.

FIG. 8 shows the % Response curves (mean ±SEM) for 3% (circles), 4% (triangles), and 5% (squares) concentrations of rabbit (N=4) red blood cells in micro-samples that contained 2 mg/ml FITC-dextran (150,000 daltons) and received a cell-attack stimulus of 210 J/cm². These % Response curves for rabbit red blood cells are statistically the same for the different micro-sample cell concentrations in the 3 to 5% range, to show that moderate variation in cell concentrations will not change the microphotolysis measurement of cell resistance to disruption by light-stimulated cell attack.

FIG. 9 shows the % Response curves (mean±SEM) for rabbit (N=3) red blood cells that had been separated from whole blood (circles) and for red blood cells in whole blood that contained plasma and other cells such as platelets or white blood cells (triangles). Micro-sample composition was a 4% red blood cell concentration and 2 mg/ml FITC-dextran (150,000 daltons). These data demonstrate that the % Response curves for rabbit red blood cells are not affected by the presence of blood plasma or other blood cells (such as white blood cells) in the micro-sample. Thus, the microphotolysis procedure can be applied to whole blood samples, without the need for careful separation of red blood cells.

FIG. 10 shows the % Response curves (mean±SEM) for microphotolysis of rabbit (N=4) red blood cells on day 5 (circles), on day 5 after the red blood cells had been washed and then reconstituted with buffer and FITC-dextran (diamonds), and on day 5 after the red blood cells had been washed and then reconstituted with buffer but not FITC-dextran (squares). Micro-sample composition was 2 mg/ml of FITC-dextran (150,000 daltons), a 4% red blood cell concentration, and buffer with a cell-attack stimulus of 198 Joules/cm². Cells that were washed on day 5 and reconstituted without the FITC-dextran did not hemolyze when exposed to photoactivation. Washed cells reconstituted with the original FITC-dextran buffer solution had the same microphotolysis response as unwashed cells on day five, thus showing that the washed cells were still responsive but only in the presence of FITC-dextran. Thus, FIG. 10 shows that the presence of FITC is necessary for the microphotolysis process and that other factors like heat from the light source do not induce hemolysis in this method. FITC-dextran (150,000) is a large molecular weight neutral dextran that does not even traverse endothelial gaps under non-inflamed conditions. Since washed cells were unresponsive, the data in FIG. 10 demonstrate that the microphotolysis response is not the result of a non-specific light interaction with an intracellular or even intramembrane bound drug. The microphotolysis process with FITC-dextran as the cell-attack agent must occur by an interaction outside of the cell membrane with subsequent effect on the cell membrane.

FIG. 11 shows the % Response curves (mean±SEM) for microphotolysis of rabbit (N=4) red blood cells that had been prepared in standard buffer with glucose and albumin (squares), buffer with glucose but not albumin (filled diamonds), buffer with albumin but not glucose (triangles), and buffer without albumin and glucose (circles). All micro-samples contained 2 mg/ml of FITC-dextran (150,000 daltons) and a 4% concentration of red blood cells, and were exposed to cell-attack stimuli of 180 J/cm² (right panel) and 90 J/cm² (left panel). The % Response curves for rabbit red blood cells are not altered by removal of albumin from the cell micro-sample. According to scientific literature, removal of albumin changes the shape of the red blood cell. Thus, these data show that the microphotolysis process measures cell characteristics other than those that depend solely on cell shape. The % Response curves are shifted to the left to reflect greater cell sensitivity to a standardized cell-attack stimulus when glucose is removed from the cell micro-sample. Cells are very susceptible (an increased Slope and decreased $T_{1/2}$) even to a very low cell-attack stimulus when glucose is absent as illustrated in the left panel of FIG. 10. According to scientific literature, glucose is necessary for cells to maintain their ATP (adenosine triphosphate) levels, and ATP is required for cell metabolism to maintain the integrity of the cell membrane. Thus, these data show that the microphotolysis process can detect a reduction in cell membrane integrity.

FIG. 12 shows the % Response curves (mean±SEM) for microphotolysis of rabbit (N=6) cell micro-samples that contained 2 mg/ml of FITC-dextran (150,000 daltons), standard buffer, and a 4% concentration of red blood cells which had been previously incubated for one hour with diamide at a concentration of 5.0 milliMolar (diamonds), 0.5 mM (squares), 0.05 mM (circles), or 0.00 mM (filled triangles), with cell-attack stimuli of 180 J/cm² (right panel) and 90 J/cm² (left panel). The % Response curves for rabbit red blood cells are shifted to the left to reflect greater cell sensitivity to a cell-attack stimulus when the micro-sample contains cells that have been previously incubated for one hour with diamide. These diamide-incubated cells have enhanced susceptibility (increased Slope and decreased $T_{1/2}$) to a very low cell-attack stimulus as illustrated in the left panel of FIG. 11. According to scientific literature, diamide is a drug which oxidizes the sulfhydryl groups of proteins in the cell membrane to increase the cross-linking of spectrin which disturbs the protein layers of the cell membrane to disrupt cell membrane integrity. Thus, these data show that the microphotolysis process can detect an increase in cell fragility which results from a disturbance to the protein layers of the cell membrane.

FIG. 13 shows the % Response curves (mean±SEM) for microphotolysis of rabbit (N=5) cell micro-samples that contained 2 mg/ml of FITC-dextran (150,000 daltons), standard buffer, and a 4% concentration of red blood cells which had been previously incubated for 20 minutes with Chlorpromazine at a concentration of 100 microMolar (circles), 30 μM (diamonds), 10 μM (squares), and 0 μM (filled triangles), with cell-attack stimuli of 180 J/cm² (right panel) and 90 J/cm² (left panel). The % Response curves for rabbit red blood cells are shifted to the left to reflect greater cell sensitivity to cell-attack when the micro-sample contains cells that have been previously incubated for 20 minutes with chlorpromazine. These chlorpromazine-incubated cells are also more susceptible (decreased $T_{1/2}$ but no change in Slope) to very low levels of cell-attack stimuli as illustrated in the left panel of FIG. 12. According to scientific literature, chlorpromazine, in the concentrations used here, primarily produces stomatocyte formation through an effect of chlorpromazine to alter the arrangement of the lipid bilayer in the cell membrane with less effect on the protein layers in the cell membrane. Thus, these data show that the microphotolysis process can detect an increase in cell membrane fragility which results from a disturbance to the lipid layers of the cell membrane.

FIG. 14 shows the % Response curves (mean±SEM) for microphotolysis of rabbit (N=6) cell micro-samples that contained 2 mg/ml FITC-dextran (150,000 daltons), standard buffer, and a 4% concentration of red blood cells which had been previously incubated for one hour with gluteraldehyde at a concentration of 0.02% (circles with dashed line), 0.01% (diamonds), 0.005% (triangles), 0.0025% (squares with dashed line), 0.00125% (circles), and 0.000% (filled triangles), with a cell-attack stimulus of 180 $J/cm^2$. The % Response curves for rabbit red blood cells are shifted to the right with increased $T_{1/2}$ and decreased Slope to reflect less cell sensitivity to a cell-attack stimulus when the micro-sample contains cells that have been previously incubated for one hour with a 0.01% or greater solution of gluteraldehyde. According to scientific literature, gluteraldehyde decreases membrane fragility (less breakable cell) and increases membrane rigidity (less deformable cell). Chlorpromazine increases membrane fragility more breakable) without any reported change in membrane rigidity (unchanged deformability). Diamide increases membrane fragility (more breakable) and increases membrane rigidity (less deformable). Thus, comparison of the effect of these three agents as shown in FIGS. 12, 13, and 14 demonstrates that the microphotolysis process measures changes in cell membrane fragility rather than simply cell membrane rigidity, and that the microphotolysis process can distinguish between a change in membrane fragility due to altered lipid layers and a change due to altered protein layers.

A streptozoticin-injected laboratory rat is a widely-used animal model of human insulin-dependent diabetes with elevated blood sugar (hyperglycemia) and glucose spill-over into the urine. Diet manipulation of a laboratory rat is a known animal model of human hypercholesterolemia. FIG. 15 shows the Percent Maximal Response (MR %) and the $T_{1/2}$ and Slope values of the % Response curves for microphotolysis of red blood cells from 5 normal control Sprague-Dawley laboratory rats (C) at 248±3.6 $J/cm^2$, 3 streptozoticin-induced insulin-dependent diabetic Sprague-Dawley rats (D) at 245±4.1 $J/cm^2$, and 6 diet-induced hypercholesterolemic Sprague-Dawley rats (H) at 249±2.7 $J/cm^2$. All cell micro-samples had a composition of 4 mg/ml FITC-dextran (20,000 daltons), standard buffer, and a 3% concentration of red blood cells. The % Response curves for red blood cells from normal rats, diabetic rats, and hypercholesterolemic rats have similar Maximal Responses to the microphotolysis process. Red blood cells from the hypercholesterolemic rats have normal $T_{1/2}$ and Slope values. Cells from the diabetic rats have significantly longer $T_{1/2}$ and lower Slope values to indicate a substantial reduction in cell membrane fragility for the diabetic animals. These data demonstrate that the microphotolysis process can detect diseases (such as diabetes) which alter ion pumps (such as the calcium pumps) in the cell membrane.

Microphotolysis of Human Cells

FIG. 16 shows the Percent Maximal Response (MR %) and the $T_{1/2}$ and Slope values of the % Response curves for microphotolysis of 0.5% to 3.0% concentrations of human (N=3) red blood cells in micro-samples that contained 4 mg/ml FITC-dextran (20,000 daltons). One subject received a cell-attack stimulus of 549±0.3 $J/cm^2$, the second subject received 340±11 $J/cm^2$ and the third subject received 198±1.3 $J/cm^2$ for all five cell concentrations. Microphotolysis of red blood cells from humans gives the same Percent Maximal Responses for micro-sample cell concentrations in the 1.0% to 3.0% range, the same $T_{1/2}$ values for cell concentrations in the 0.5% to 2.0% range, and the same % Response curve Slopes for cell concentrations in the 0.5% to 3% range as shown in FIG. 16. Microphotolysis of red blood cells from rabbits gives the same % Response curves for micro-sample cell concentrations in the 3% to 5% range as illustrated in FIG. 8. These data indicate that the microphotolysis process is relatively insensitive to variations in cell concentrations within specific but different concentration ranges for animals and humans.

According to scientific literature, pentoxifylline, a therapeutic agent which increases peripheral blood flow in several human pathologies, increases the "flexibility" of cell membranes to permit easier passage of red blood cells through blood vessels; yet, pentoxifylline does not simply alter cell membrane rigidity (cell deformability). FIG. 17 shows the Percent Maximal Response (MR %) and the $T_{1/2}$ and Slope values of the % Response curves for microphotolysis of human (N=5) cell micro-samples that contained 4 mg/ml FITC-dextran (20,000 daltons) and a 1% concentration of red blood cells which had been previously incubated at 4° C. FOR ONE HOUR with pentoxifylline (PTFX) concentrations of 10 milliMolar (filled bars), 1 mM (striped bars), and 0 mM (clear bars). One subject received a cell-attack stimulus of 658±6.6 $J/cm^2$, three subjects received 329±1.9 $J/cm^2$, and one subject received 196±0.7 $J/cm^2$ for all three pentoxifylline concentrations. FIG. 18 shows the Percent Maximal Response (MR %) and the $T_{1/2}$ and Slope values of the % Response curves for microphotolysis of human (N=5) cell micro-sample that contained 4 mg/ml FITC-dextran (20,000 daltons) and a 1% concentration of red blood cells which had been previously incubated at 4° C. FOR TWENTY-FOUR HOURS with pentoxifylline (PTFX) concentrations of 10 milliMolar (filled bars), 1 mM (striped bars), and 0 mM (clear bars). One of these subjects received a cell-attack stimulus of 641±3.3 $J/cm^2$, three subjects received 330±1.7 $J/cm^2$, and one subject received 205±0.7 $J/cm^2$ for all three pentoxifylline concentrations. Incubation of human red blood cells with pentoxifylline for one hour alters the microphotolysis response of those cells. As the pentoxifylline concentration is increased, there is a progressive (dose-dependent) decrease in the Percent Maximal Response, an increase in $T_{1/2}$, and a decrease in the Slope of the microphotolysis % Response curves as illustrated in FIG. 17. With 24-hour pentoxifylline incubation of red blood cells as shown in FIG. 18, the decrease in the Percent Maximal Response is lost, and the decrease in Slope is partially lost, but the dose-dependent increase in $T_{1/2}$ is still present. These data demonstrate that the microphotolysis process is sensitive to drug-induced alterations in human cell membranes, and that microphotolysis can distinguish between drug-treated and non-treated human cells, as a function of time after drug treatment.

FIG. 19 shows the Percent Maximal Response (MR %) and the $T_{1/2}$ and Slope values of the % Response curves at cell-attack stimuli of A=243±2.9 $J/cm^2$ (clear bars), B=400±3.6 $J/cm^2$ (striped bars), and C=642±4.0 $J/cm^2$ (filled bars) for microphotolysis of red blood cells from four female and three male African-Americans who had no clinical indicators of sickle-cell disease. The cell microsamples contained 4 mg/ml FITC-dextran (20,000 daltons), a 3% concentration of red blood cells, and buffer. FIG. 20 shows the Percent Maximal Response (MR %) and the $T_{1/2}$ and Slope values of the % Response curves at cell-attack stimuli of A=247±1.1J/cm$^2$ (clear bars), B=395±5.5 J/cm$^2$ (striped bars), and C=643±4.0 J/cm$^2$ (filled bars) for microphotolysis of red blood cells from 2 female and 3 male African-Americans with clinical diagnosis of sickle-cell disease but not hemoglobin-F abnormality. The cell microsamples contained 4 mg/ml FITC-dextran (20,000 daltons), a 3% concentration of red blood cells, and buffer. Normal red blood cells from humans without sickle-cell disease as illustrated in the left panel of FIG. 19 show an eventual 88 to 95% disruption (Percent Maximal Response, MR %) after exposure to cell-attack stimuli across a broad range from 240 J/cm$^2$ to 660 J/cm$^2$. These normal human cells have microphotolysis % Response curves with a progressively decreasing $T_{1/2}$ and a progressively increasing Slope as the cell-attack stimulus is increased as shown in FIG. 19. In contrast, red blood cells from humans with sickle-cell disease have a substantially reduced Percent Maximal Response (with a peak at an intermediate cell-attack stimulus level), a significantly elevated $T_{1/2}$ which is not a function of cell-attack stimulus level, and a substantially reduced Slope as is evident in a comparison of FIG. 20 to FIG. 19. These data demonstrate that the microphotolysis process is sensitive to pathologic alterations in human cell membranes, and that microphotolysis provides multiple parameters for detection of human diseases that alter cells.

FIG. 21 shows the Percent Maximal Response (MR %) and the $T_{1/2}$ and Slope values of the % Response curves at cell-attack stimuli of A=253±2.8 J/cm$^2$ (clear bars), B=399±4.6 J/cm$^2$ (striped bars), and C=661±2.1J/cm$^2$ (filled bars) for microphotolysis of red blood cells from 1 female and 1 male African-American with clinical diagnosis of sickle-cell disease and hemoglobin-F abnormality. The cell micro-samples contained 4 mg/ml FITC-dextran (20,000 daltons), a 3% concentration of red blood cells, and buffer. Red blood cells from humans with a combination of sickle-cell disease and a hemoglobin-F abnormality have a normal Percent Maximal Response, an abnormally high $T_{1/2}$, and a normal Slope at lower cell-attack stimuli but a reduced Slope at the higher cell-attack stimulus as is evident in a comparison of FIG. 21 to FIG. 19. These data show that the microphotolysis process is sensitive to combinations of pathologic alterations in human cell membranes. Also these data demonstrate that multiple parameters of the microphotolysis process can differentiate between normal human cells as shown in FIG. 19 and single-disease altered cells as shown in FIG. 20, and can distinguish both of those situations from multiple abnormalities such as those shown in FIG. 21.

The foregoing detailed description is given primarily for clearness of understanding and no unnecessary limitations are to be understood therefrom, for modifications will become obvious to those skilled in the art based upon more recent disclosures and may be made without departing from the spirit of the invention and scope of the appended claims.

I claim:

1. A microphoto lysis-analysis process for measuring the strength of a cell membrane and detecting abnormalities thereof by applying precise quantities of a first focused light of selected frequency and energy density to a precise microscopic area of a cell sample containing test cells for measuring as a function of time the precise degree of cell disruption, applying a second focused light of second selected frequency and energy density to said cell sample thereby photo-activating a light activated cell-attack fluorochrome for attacking cell membranes in said microscopic area of light-stimulated cell-attack providing a quantitative, time-related, light-dose dependent measure of cell fragility, comprising the steps of:

suspending test cells whose membrane strength are to be measured in a physiologic salt solution of selected osmolality forming a cell containing solution;

adding an inactive light activated cell-attack fluorochrome to said cell containing solution, said inactive cell-attack fluorochrome comprising molecules absorbing light energy in a known range of excitation frequencies producing a photosensitive chemical solution;

preparing a micro-sample of said photosensitive chemical solution containing said test cells;

identifying a localized microscopic area within said micro-sample of said photosensitive solution;

applying a specific amount of the focused first frequency-specific light energy in the cell absorption range to said micro-sample of said photosensitive chemical solution, exposing said cell(s) in said photosensitive chemical solution to said first frequency-specific light energy for a selected period of time for determining light absorption by intact test cells in said localized microscopic area of said micro-sample at any time period;

determining the light absorption and number of intact test cells in said localized microscopic area by measuring the amount of said first frequency-specific light energy passing through said cells in said micro-sample of said photosensitive chemical solution in said localized microscopic area;

applying a specific amount of the focused second frequency-specific light energy in the fluorochrome-excitation range for a selected time in a selected time interval at a selected different wavelength than said first frequency-specific light energy, said second frequency-specific light energy photo-activating said photosensitive chemical solution forming a cell-reacting medium;

reacting said cell-reacting medium containing said test cells in said localized microscopic area disrupting the cell membranes of said test cells permitting loss of said cell contents and changing the absorption of said first frequency-specific light energy by said test cells in said localized microscopic area;

analyzing the strength of said cell membrane quantitatively by comparing the amount of said first frequency-specific light energy passing through said test cells in said micro-sample after micro-sample exposure to said second frequency-specific light energy, with the amount of said first frequency-specific light energy passing through said test cell(s) in said micro-sample before micro-sample exposure to said second frequency-specific light energy for determining light absorption by remaining intact test cells in said localized microscopic area at selected time intervals; and coordinating and comparing the above test results to values for normal cell(s) to measure changes in cell fragility.

2. The microphoto lysis-analysis process for measuring the strength of a cell membrane as claimed in claim 3, wherein said analyzing step comprises comparing the starting number of cells with the maximum number of test cells disrupted, the time to reach disruption of ½ of the maximum number of cells to be disrupted, and the maximum rate of cell disruption during said selected time intervals.

3. The microphoto lysis-analysis process for measuring the strength of a cell membrane as claimed in claim 1, including the step of selecting said test cells from the group consisting of red cells, white cells, platelets, or mixture thereof.

4. The microphoto lysis-analysis process for measuring the strength of a cell membrane as claimed in claim 1, including the step of suspending test cells whose membrane strength is to be measured in a physiologic solution of selected osmolality ranging from about 295 to about 315 milliosmoles forming a cell containing solution.

5. The microphoto lysis-analysis process for measuring the strength of a cell membrane as claimed in claim 1, including the step of applying said focused first frequency-specific light energy in time intervals ranging from about 2 minutes to about 60 minutes.

6. The microphoto lysis-analysis process for measuring the strength of a cell membrane as claimed in claim 1, including the step of applying said focused second frequency-specific light energy in time intervals ranging from about 2 minutes to about 10 minutes.

7. The microphoto lysis-analysis process for measuring the strength of a cell membrane as claimed in claim 1, including the step of applying and measuring the amount of said focused first frequency-specific light energy passing through said micro-sample at 30-second time intervals over a 60-minute period or until there are 5 or fewer intact test cells within said localized microscopic area.

8. The microphoto lysis-analysis process for measuring the strength of a cell membrane as claimed in claim 1, including the step of preparing a micro-sample of about 25 microliters (µl) of said photosensitive chemical solution.

9. The microphoto lysis-analysis process for measuring the strength of a cell membrane as claimed in claim 3, including the step of applying a second frequency-specific light energy at a selected different wavelength to photo-activate said inactive cell-attack fluorochrome from about 2 minutes to about 10 minutes depending on the particular inactive cell-attack fluorochrome selected.

10. The microphoto lysis-analysis process for measuring the strength of a cell membrane as claimed in claim 1, further including the step of selecting said light activated cell-attack fluorochrome specific to the type of cell to be analyzed.

11. The microphoto lysis-analysis process for measuring the strength of a cell membrane as claimed in claim 1, further including the step of selecting said light activated cell-attack fluorochrome from the group consisting of phloxine B, eosin-isothiocyanate, pheophorbide, protoporphyrin, fluorescein isothiocyanate, fluorescein isothiocyanate dextran, and combinations thereof.

12. The microphoto lysis-analysis process for measuring the strength of a cell membrane as claimed in claim 1, further including the step of adding diamide to said cell containing solution for oxidizing the sulfhydryl groups of proteins in the cell membrane to increase membrane fragility and for increasing the cross-linking of spectrin to increase membrane rigidity disrupt cell membrane integrity inducing alterations in cell membranes for determining the effect of said diamide on cell response to micro-photo lysis by applying a standardized light activated cell-attack fluorochrome and distinguishing between diamide-treated and nontreated cells as a function of time after diamide treatment.

13. The microphoto lysis-analysis process for measuring the strength of a cell membrane as claimed in claim 1, further including the step of adding chlorpromazine to said cell containing solution producing stomatocytes and altering the lipid bilayer of said cell membranes to disrupt cell membrane integrity by increasing membrane fragility without any change in rigidity of said cell membrane inducing alterations in cell membranes for determining the effect of said chlorpromazine on cell response to microphoto lysis by applying a standardized light activated cell-attack fluorochrome and distinguishing between cholorpromazine treated and nontreated cells as a function of time after chlorpromazine treatment.

14. The microphoto lysis-analysis process for measuring the strength of a cell membrane as claimed in claim 1, further including the step of adding glutaraldehyde to said cell containing solution decreasing membrane fragility and increasing membrane rigidity of said cell membrane inducing alterations in cell membranes for determining the effect of said glutaraldehyde on cell response to microphoto lysis by applying a standardized light activated cell-attack fluorochrome and distinguishing between glutararaldehyde treated and nontreated cells as a function of time after glutaraldehyde treatment.

15. The microphoto lysis-analysis process for measuring the strength of a cell membrane as claimed in claim 1, further comprising the step of selecting human red blood cells as said test cells and comparing said selected red blood cells with control cells for detecting the disease diabetes by changes in the cell response to microphoto lysis for changes in membrane integrity caused by said disease.

16. The microphoto lysis-analysis process for measuring the strength of a cell membrane as claimed in claim 1, further comprising the step of determining the level of ATP (adenosine triphosphate) in a cell sample by treating the cell sample with known concentrations of said ATP inducing alterations in cell membranes of the cell sample for determining the effect of said addition of said ATP on cell response to microphoto lysis by applying a standardized light activated cell-attack fluorochrome to the cell sample and distinguishing between the integrity of the ATP affected cells and untreated cells before and after the addition of ATP as a function of time after treatment and comparing the membrane integrity of cells in the untreated cell sample with the membrane integrity of human red blood cells in the ATP-treated cell sample.

17. The microphoto lysis-analysis process for measuring the strength of a cell membrane as claimed in claim 1, further comprising the step of selecting human red blood cells as said test cells and comparing said selected red blood cells with control human blood cells for detecting the disease sickle-cell anemia by changes in the cell response to microphoto lysis for changes in cell membrane integrity caused by said disease.

18. The microphoto lysis-analysis process for measuring the strength of a cell membrane as claimed in claim 1, further including the step of selecting a specific light activated cell-attack fluorochrome for a specific type of test cell.

19. The microphoto lysis-analysis process for measuring the strength of a cell membrane as claimed in claim 1, including the step of standardizing said osmolality of said test cells and light activated cell-attack fluorochrome in a standardized buffer solution.

20. The microphoto lysis-analysis process for measuring the strength of a cell membrane as claimed in claim 1, including the step of varying the concentration of said test cells suspended in said cell containing solution.

21. The microphoto lysis-analysis analysis process for measuring the strength of a cell membrane as claimed in claim 1, which comprises the steps of testing for a cell membrane altering disease including diabetes, hypercholesterolemia, and sickle-cell anemia.

22. The microphoto lysis-analysis process for measuring the strength of a cell membrane as claimed in claim 1, further including the step of adding an extracellular membrane-bound specific test drug to said cell containing solution for measuring alterations in cell membrane fragility due to changes in membrane characteristics that are created by a light activated cell-attack fluorochrome that remains and becomes activated only outside the cell.

23. The microphoto lysis-analysis process for measuring the strength of a cell membrane as claimed in claim 1, further including the step of preparing a micro-sample of about 25 microliters (µl) of said photosensitive chemical solution within a covered well means and placing at least one water saturated wick within said well means in close proximity to said micro-sample for preventing dehydration of said micro-sample of said photosensitive chemical solution.

24. The microphoto lysis-analysis process for measuring the strength of a cell membrane as claimed in claim 1, further comprising the step of determining the level of glucose in the cell containing sample by treating the cell containing sample with known amounts of glucose and comparing the membrane integrity of test cells in the untreated cell containing sample with the membrane integrity of test cells in the treated cell containing sample.

25. The microphoto lysis-analysis process for measuring the strength of a cell membrane as claimed in claim 1, wherein said analyzing step comprises comparing the starting number of test cells with the maximum number of cells disrupted, the time to reach disruption of ½ of the maximum number of cells to be disrupted, and the maximum rate of cell disruption.

26. The microphoto lysis-analysis process for measuring the strength of a cell membrane as claimed in claim 25, including the step of producing a cell-response curve having at least four different quantitative measurements of cell membrane integrity for said selected time intervals of cell response to a light activated cell-attack fluorochrome.

27. The microphoto lysis-analysis process for measuring the strength of a cell membrane as claimed in claim 1, comprising the step of adding a test substance to said cell containing solution providing test substance induced alterations in cell membranes for determining the effect of said test substance on cell response to microphoto lysis by applying a standardized light-activated cell-attack fluorochrome and distinguishing between test substance treated and nontreated cells as a function of time after test substance treatment, said test substance being selected from the group consisting of glutaraldehyde, albumin, chlorpromazine, diamide, glucose, albumin, and pentoxyifylline.

28. The microphoto lysis-analysis process for measuring the strength of a cell membrane as claimed in claim 27, further including the step of comparing the effect of adding at least one test substance to said cell containing solution for measuring the effect of said test substance on changes in said cell membrane fragility and distinguishing between a change in said membrane fragility due to altered lipid layers and a change in said membrane fragility due to altered protein layers of said cell membrane.

29. The microphoto lysis-analysis process for measuring the strength of a cell membrane as claimed in claim 1, further comprising the step of selecting human red blood cells as said test cells and comparing said selected red blood cells with control human blood cells for detecting pathologic alterations in human cells membranes by changes in the cell response to microphoto lysis for changes in the cell membrane integrity caused by the said membrane pathology.

30. The microphoto lysis-analysis process for measuring the strength of a cell membrane as claimed in claim 29, further comprising the step of selecting human red blood cells as said test cells and comparing said selected red blood cells with control human blood cells for differentiating between normal human cells and single-disease altered cells and for distinguishing said normal human cells and said single-disease altered cells from multiple disease altered cells.

31. The microphoto lysis-analysis process for measuring the strength of a cell membrane as claimed in claim 1, including the step of applying said focused second frequency-specific light energy to produce a pattern of changes for untreated normal cells with normal membranes and normal metabolism and comparing the strength of the membrane of said untreated normal cells with the strength of the membrane of cells which have been treated by exposure to a known chemical.

32. The microphoto lysis-analysis process for measuring the strength of a cell membrane as claimed in claim 31, which comprises the steps of adding a chemical which alters a cell membrane including pentoxifylline, diamide, glutaraldehyde, and chlorpromazine.

33. The microphoto lysis-analysis process for measuring the strength of a cell membrane as claimed in claim 1, further including the step of adding a test drug to said cell containing solution providing drug-induced alterations in cell membranes for determining the effect of said test drug on cell response microphoto lysis by applying a standardized light-activated cell-attack fluorochrome and distinguishing between drug-treated and nontreated cells as a function of time after drug treatment.

34. The microphoto lysis-analysis process for measuring the strength of a cell membrane as claimed in claim 33, further comprising the steps of detecting drug-induced alterations in human cell membranes of a cell sample containing an unknown concentration of a said drug by adding known concentrations of said drug to the cell sample inducing alterations in cell membranes for determining the effect of said addition of known concentration of said drug on cell response to microphoto lysis by applying a standardized light activated cell-attack fluorochrome before and after the addition of the known concentration of drug.

35. The microphoto lysis-analysis process for measuring the strength of a cell membrane as claimed in claim 33, wherein said test drug is an intracellular-bound specific test drug.

36. The microphoto lysis-analysis process for measuring the strength of a cell membrane as claimed in claim 35, further including the step of adding an intracellular membrane-bound specific test drug to said cell containing solution for measuring alterations in cell membrane fragility due to changes in membrane characteristics that are created by a light activated cell-attack fluorochrome that processes through the cell membrane to attach to internal cell structures where said fluorochrome becomes activated only inside of the cell.

37. A microphoto lysis-analysis process for measuring the strength of a cell membrane and detecting abnormalities thereof by applying precise quantities of a first focused light of selected frequency and energy density to a precise microscopic area of a cell sample containing test cells for measuring as a function of time the precise degree of cell disruption, applying a second focused light of second selected frequency and energy density to said cell sample thereby photo-activating a light activated cell-attack fluorohrome for attacking cell membranes in said microscopic area of light-stimulated cell-attack providing a quantitative, time-related, light-dose dependent measure of cell fragility, comprising the steps of:

suspending test cells whose membrane strength are to be measured in a cell containing solution;

adding an inactive light activated cell-attack fluorochrome to said cell containing solution, said inactive cell-attack fluorochrome comprising molecules absorbing light energy in a known range of excitation frequencies producing a photosensitive chemical solution;

preparing a micro-sample of said photosensitive chemical solution containing said test cells;

identifying a localized microscopic area within said micro-sample of said photosensitive solution;

applying a specific amount of the focused first frequency-specific light energy in the cell absorption range to said micro-sample of said photosensitive chemical solution, exposing said cell(s) in said photosensitive chemical solution to said first frequency-specific light energy for a selected period of time for determining light absorption by intact test cells in said localized microscopic area of said micro-sample at any time period;

determining the light absorption and number of intact test cells in said localized microscopic area by measuring the amount of said first frequency-specific light energy passing through said cells in said micro-sample of said photosensitive chemical solution in said localized microscopic area;

applying a specific amount of the focused second frequency-specific light energy in the fluorochrome-excitation range for a selected time in a selected time interval at a selected different wavelength than said first frequency-specific light energy, said second frequency-specific light energy photo-activating said photosensitive chemical solution forming a cell-reacting medium;

reacting said cell-reacting medium containing said test cells in said localized microscopic area disrupting the cell membranes of said test cells permitting loss of said cell contents and changing the absorption of said first frequency-specific light energy by said test cells in said localized microscopic area;

analyzing the strength of said cell membrane quantitatively by comparing the amount of said first frequency-specific light energy passing through said test cells in said micro-sample after micro-sample exposure to said second frequency-specific light energy, with the amount of said first frequency-specific light energy passing through said test cell(s) in said micro-sample before micro-sample exsposure to said second frequency-specific light energy for determining light absorption by remaining intact test cells in said localized microscopic area at selected time intervals; and coordinating and comparing the above test results to values for normal cell(s) to measure changes in cell fragility.

38. The microphoto lysis-analysis process for measuring the strength of a cell membrane as claimed in claim 37, wherein said analyzing step comprises comparing the starting number of cells with the maximum number of test cells disrupted, the time to reach disruption of ½ of the maximum number of cells to be disrupted, and the maximum rate of cell disruption during said selected time intervals.

39. The microphoto lysis-analysis process for measuring the strength of a cell membrane as claimed in claim 37 including the step of selecting said test cells from the group consisting of red cells, white cells, platelets, or mixture thereof.

40. The microphoto lysis-analysis process for measuring the strength of a cell membrane as claimed in claim 37, including the step of applying said focused first frequency-specific light energy in time intervals ranging from about 2 minutes to about 60 minutes.

41. The microphoto lysis-analysis process for measuring the strength of a cell membrane as claimed in claim 37 including the step of applying said focused second frequency-specific light energy in time intervals ranging from about 2 minutes to abut 10 minutes.

42. The microphoto lysis-analysis process for measuring the strength of a cell membrane as claimed in claim 37, including the step of applying and measuring the amount of said focused first frequency-specific light energy passing through said micro-sample at 30-second time intervals over a 60-minute period or until there are 5 or fewer intact test cells within said localized microscopic area.

43. The microphoto lysis-analysis process for measuring the strength of a cell membrane as claimed in claim 37, including the step of preparing a micro-sample of about 25 microliters (μl) of said photosensitive chemical solution.

44. The microphoto lysis-analysis process for measuring the strength of a cell membrane as claimed in claim 37, including the step of applying a second frequency-specific light energy at a selected different wavelength to photo-activate said inactive cell-attack fluorochrome from about 2 minutes to about 10 minutes depending on the particular inactive cell-attack fluorochrome selected.

45. The microphoto lysis-analysis process for measuring the strength of a cell membrane as claimed in claim 37, further including the step of selecting said light activated cell-attack fluorochrome specific to the type of cell to be analyzed.

46. The microphoto lysis-analysis process for measuring the strength of a cell membrane as claimed in claim 37, further including the step of selecting said light activated cell-attack fluorochrome from the group consisting of phloxine B, eosinieothiocyanate, pheophorbide, protoporphyrin, fluorescein isothiocyanate, fluorescein isothiocyanate dextran, and combinations thereof.

47. The microphoto lysis-analysis process for measuring the strength of a cell membrane as claimed in claim 37, further including the step of adding diamide to said cell containing solution fox oxidizing the sulfhydryl groups of proteins in the cell membrane to increase membrane fragility and for increasing the cross-linking of spectrin to increase membrane rigidity and disrupt cell membrane integrity inducing alterations in cell membranes for determining the effect of said diamide on cell response to micro-photo lysis by applying a standardized light activated cell-attack fluorochrome and distinguishing between diamide-treated and nontreated cells as a function of time after diamide treatment.

48. The microphoto lysis-analysis process for measuring the strength of a cell membrane as claimed in claim 37, further including the step of adding chlorpromazine to said cell containing solution producing stomatocytes and altering the lipid bilayer of said cell membranes to disrupt cell membrane integrity by increasing membrane fragility without any change in rigidity of said cell membrane inducing alterations in cell membranes for determining the effect of said chlorpromazine on cell response to microphoto lysis by applying a standardized light activated cell-attack fluorochrome and distinguishing between chlorpromazine treated and nontreated cells as a function of time after chlorpromazine treatment.

49. The microphoto lysis-analysis process for measuring the strength of a cell membrane as claimed in claim 37, further including the step of adding glutaraldehyde to said cell containing solution decreasing membrane fragility and increasing membrane rigidity of said cell membrane inducing alterations in cell membranes for determining the effect of said glutaraldehyde on cell response to microphoto lysis by applying a standardized light activated cell-attack fluorochrome and distinguishing between glutaraldehyde treated and nontreated cells as a function of time after glutaraldehyde treatment.

50. The microphoto lysis-analysis process for measuring the strength of a cell membrane as claimed in claim 37, further comprising the step of selecting human red blood cells as said test cells and comparing said selected red blood cells with control cells for detecting the disease diabetes by changes in the cell response to microphoto lysis for changes in membrane integrity caused by said disease.

51. The microphoto lysis-analysis process for measuring the strength of a cell membrane is claimed in claim 37, further comprising the step of determining the level of ATP (adenosine triphosphate) in a cell sample by treating the cell sample with known concentrations of said ATP inducing alterations in cell membranes of the cell sample for determining the effect of said addition of said ATP on cell response to microphoto lysis by applying a standardized light activated cell-attack fluorochrome to the cell sample and distinguishing between the integrity of the ATP affected cells and untreated cells before and after the addition of ATP as a function of time after treatment and comparing the membrane integrity of cells in the untreated cell sample with the membrane integrity of human red blood cells in the ATP-treated cell sample.

52. The micro lysis-analysis process for measuring the strength of a cell membrane as claimed in claim 37, further comprising the step of selecting human red blood cells as said test cells and comparing said selected red blood cells with control human blood cells for detecting the disease sickle-cell anemia by changes in the cell response to microphoto lysis for changes in cell membrane integrity caused by said disease.

53. The microphoto lysis-analysis process for measuring the strength of a cell membrane as claimed in claim 37, further including the step of selecting a specific light activated cell-attack fluorochrome for a specific type of test cell.

54. The microphoto lysis-analysis process for measuring the strength of a cell membrane as claimed in claim 37, including the step of varying the concentration of said test cells suspended in said cell containing solution.

55. The microphoto lysis-analysis process for measuring the strength of a cell membrane as claimed in claim 37, which comprises the steps of testing for a cell membrane altering disease including diabetes, hypercholesterolemia, and sickle-cell anemia.

56. The microphoto lysis-analysis process for measuring the strength of a cell membrane as claimed in claim 37, further including the step of adding an extracellular membrane-bound specific test drug to said cell containing solution for measuring alterations in cell membrane fragility due to changes in membrane characteristics that are created by a light activated cell-attack fluorochrome that remains and becomes activated only outside the cell.

57. The microphoto lysis-analysis process for measuring the strength of a cell membrane as claimed in claim 37, further including the step of preparing a micro-sample of about 25 microliters ($\mu$l) of said photosensitive chemical solution within a covered well means and placing at least one water saturated wick within said well means in close proximity to said micro-sample for preventing dehydration of said micro-sample of said photosensitive chemical solution.

58. The microphoto lysis-analysis process for claim 37, measuring the strength of a cell membrane as claimed in further comprising the step of determining the level of glucose in the cell containing sample by treating the cell containing sample with known amounts of glucose and comparing the membrane integrity of test cells in the untreated cell containing sample with the membrane integrity of test cells in the treated cell containing sample.

59. The microphoto lysis-analysis process for measuring the strength of a cell membrane as claimed in claim 37, wherein said analysing step comprises comparing the starting number of test cells with the maxium number of cells disrupted, the time to reach disruption of ½ of the maximum number of cells to be disrupted, and the maximum rate of cell disruption.

60. The microphoto lysis-analysis process for measuring the strength of a cell membrane as claimed in claim 59, including the step of producing a cell-response curve having at least four different quantitative measurements of cell membrane integrity for said selected time intervals of cell response to a light activated cell-attack fluorochrome.

61. The microphoto lysis-analysis process for measuring the strength of a cell membrane as claimed in claim 37, further comprising the step of selecting human red blood cells as said test cells and comparing said selected red blood cells with control human blood cells for detecting pathologic alterations in human cell membranes by changes in the cell response to microphoto lysis for changes in the cell membrane integrity caused by the said membrane pathology.

62. The microphoto lysis-analysis process for measuring the strength of a cell membrane as claimed in claim 61, further comprising the step of selecting human red blood cells as said test cells and comparing said selected red blood cells with control human blood cells for differentiating between normal human cells and single-disease altered cells and for distinguishing said normal human cells and said single-disease altered cells from multiple disease altered cells.

63. The microphoto lysis-analysis process for measuring the strength of a cell membrane as claimed in claim 37, including the step of applying said focused second frequency-specific light energy to produce a pattern of changes for untreated normal cells with normal membranes and normal metabolism and comparing the strength of the membrane of said untreated normal cells with the strength of the membrane of cells which have been treated by exposure to a known chemical.

64. The microphoto lysis-analysis process for measuring the strength of a cell membrane as claimed in claim 63, which comprises the steps of adding a chemical which alters a cell membrane including pentoxifylline, diamide, glutaraldehyde, and chlorpromazine.

65. The microphoto lysis-analysis process for measuring the strength of a cell membrane as claimed in claim 37, comprising the step of adding a test substance to said cell containing solution providing test substance induced alterations in cell membranes for determining the effect of said test substance on cell response to microphoto lysis by applying a standardized light-activated cell-attack fluorochrome and distinguishing between test substance treated and nontreated cells as a function of time after test substance treatment, said test substance being selected from the group consisting of glutaraldehyde, albumin, chlorpromazine, diamide, glucose, albumin, and pentoxifyline.

66. The microphoto lysis-analysis process for measuring the strength of a cell membrane as claimed in claim 65, further including the step of comparing the effect of adding at least one test substance to said cell containing solution for measuring the effect of said test substance on changes in said cell membrane fragility and distinguishing between a change in said membrane fragility due to altered lipid layers and a change in said membrane fragility due to altered protein layers of said cell membrane.

67. The microphoto lysis-analysis process for measuring the strength of a cell membrane as claimed in claim 43, further including the step of adding a test drug to said cell containing solution providing drug-induced alterations in cell membranes for determining the effect of said test drug on cell response to microphoto lysis by applying a standardized light-activated cell-attack fluorochrome and distinguishing between drug-treated and nontreated cells as a function of time after drug treatment.

68. The microphoto lysis-analysis process for measuring the strength of a cell membrane as claimed in claim 67, further comprising the steps of detecting drug-induced alterations in human cell membranes of a cell sample containing an unknown concentration of a said drug by adding known concentrations of said drug to the cell sample inducing alterations in cell membranes for determining the effect of said addition of known concentration of said drug on cell response to microphoto lysis by applying a standardized light activated cell-attack fluorochrome before and after the addition of the known concentration of drug.

69. The microphoto lysis-analysis process for measuring the strength of a cell membrane as claimed in claim 67, wherein said test drug is an intracellular-bound specific test drug.

70. The microphoto lysis-analysis process for measuring the strength of a cell membrane as claimed in claim 69, further including the step of adding an intracellular membrane-bound specific test drug to said cell containing solution for measuring alterations in cell membrane fragility due to changes in membrane characteristics that are created by a light activated cell-attack fluorochrome that processes through the cell membrane to attach to internal cell structures where said fluorochrome becomes activated only inside of the cell.

* * * * *